United States Patent
Gimbel et al.

(10) Patent No.: US 8,940,051 B2
(45) Date of Patent: Jan. 27, 2015

(54) INTERBODY DEVICE INSERTION SYSTEMS AND METHODS

(71) Applicant: Flexuspine, Pittsburgh, PA (US)

(72) Inventors: Jonathan A. Gimbel, Murrysville, PA (US); Michael S. Schular, Pittsburgh, PA (US); Erik J. Wagner, Austin, TX (US); Scott Koysh, Carnegie, PA (US)

(73) Assignee: Flexuspine, Inc., Coraopolis, PA (US)

( * ) Notice: Subject to any disclaimer, the term of this patent is extended or adjusted under 35 U.S.C. 154(b) by 137 days.

(21) Appl. No.: 13/784,224

(22) Filed: Mar. 4, 2013

(65) Prior Publication Data

US 2013/0245769 A1    Sep. 19, 2013

Related U.S. Application Data

(63) Continuation of application No. 13/072,511, filed on Mar. 25, 2011, now Pat. No. 8,388,687.

(51) Int. Cl.
*A61F 2/44* (2006.01)
*A61F 2/46* (2006.01)
(Continued)

(52) U.S. Cl.
CPC .............. *A61F 2/4425* (2013.01); *A61F 2/4405* (2013.01); *A61F 2/4611* (2013.01);
(Continued)

(58) Field of Classification Search
CPC ... A61F 2/4405; A61F 2/4425; A61F 2/4611; A61F 2/4684; A61F 2002/4687; A61F 2002/30825; A61F 2/30767; A61F 2002/30079; A61F 2002/3008; A61F 2002/30387; A61F 2002/30392; A61F 2002/30393; A61F 2002/30492; A61F 2002/30563; A61F 2002/30579; A61F 2002/30594; A61F 2002/30616; A61F 2002/30617; A61F 2002/30624; A61F 2002/30639; A61F 2002/3082; A61F 2002/30841; A61F 2002/30878; A61F 2002/30884; A61F 2002/30904; A61F 2002/443; A61F 2002/448; A61F 2002/4628; A61F 2002/4629; A61F 2220/0025; A61F 2250/0098; A61F 2310/00017; A61F 2310/00023; A61F 2310/00958; A61F 2310/00976; A61F 2002/30823; A61B 17/702

USPC ............ 623/17.11–17.16; 606/246–249, 104, 606/90, 99, 86 A; 128/898
See application file for complete search history.

(56) References Cited

U.S. PATENT DOCUMENTS 3,848,601 A   11/1974  Ma et al.
3,867,728 A   2/1975   Substad et al.
(Continued)

FOREIGN PATENT DOCUMENTS

WO   2006002359   1/2006
WO   2006057698   6/2006
(Continued)

OTHER PUBLICATIONS

U. S. P.T. O. Non-Final Office Action for U.S. Appl. No. 13/437,604, mailed Jul. 2, 2014.
(Continued)

*Primary Examiner* — Pedro Philogene
(74) *Attorney, Agent, or Firm* — Meyertons, Hood, Kivlin, Kowert & Goetzel, P.C.; Eric B. Meyertons

(57) ABSTRACT

Provided is a system for implanting an interbody device into a disc space located between a first and second vertebra includes a guide frame including a guide member having an opening. The system further includes an implant trial including an elongated body and a base plate coupled to the elongated body. The elongated body of the implant trial is releasably coupled to the guide member of the guide frame during use such that the opening guides longitudinal movement of the implant trial relative to the guide frame. The system still further includes a dilator operatively coupled to the elongated body during use for distracting the disc space. The system still further includes an insertion instrument including an elongated body and an insertion member coupled to the elongated body. The elongated body of the insertion instrument is releasably coupled to the guide member of the guide frame during use such that the opening guides longitudinal movement of the insertion instrument relative to the guide frame. The insertion member is releasably coupled to at least a portion of the interbody device during use.

21 Claims, 15 Drawing Sheets

(51) Int. Cl.
  *A61F 2/30* (2006.01)
  *A61B 17/70* (2006.01)
(52) U.S. Cl.
  CPC ......... *A61F2/4684* (2013.01); *A61F 2/30767* (2013.01); *A61F 2002/30079* (2013.01); *A61F 2002/3008* (2013.01); *A61F 2002/30387* (2013.01); *A61F 2002/30392* (2013.01); *A61F 2002/30393* (2013.01); *A61F 2002/30492* (2013.01); *A61F 2002/30563* (2013.01); *A61F 2002/30579* (2013.01); *A61F 2002/30594* (2013.01); *A61F 2002/30604* (2013.01); *A61F 2002/30616* (2013.01); *A61F 2002/30617* (2013.01); *A61F 2002/30624* (2013.01); *A61F 2002/30639* (2013.01); *A61F 2002/3082* (2013.01); *A61F 2002/30841* (2013.01); *A61F 2002/30878* (2013.01); *A61F 2002/30884* (2013.01); *A61F 2002/30904* (2013.01); *A61F 2002/443* (2013.01); *A61F 2002/448* (2013.01); *A61F 2002/4628* (2013.01); *A61F 2002/4629* (2013.01); *A61F 2002/4658* (2013.01); *A61F 2220/0025* (2013.01); *A61F 2250/0098* (2013.01); *A61F 2310/00017* (2013.01); *A61F 2310/00023* (2013.01); *A61F 2310/00958* (2013.01); *A61F 2310/00976* (2013.01); *A61F 2002/30823* (2013.01); *A61F 2002/30825* (2013.01); *A61B 17/702* (2013.01); *A61F 2002/4687* (2013.01)
  USPC .................................................... 623/17.16

(56) References Cited

U.S. PATENT DOCUMENTS

| | | | |
|---|---|---|---|
| 4,309,777 | A | 1/1982 | Patil |
| 4,349,921 | A | 9/1982 | Kuntz |
| 4,611,581 | A | 9/1986 | Steffee |
| 4,657,550 | A | 4/1987 | Daher |
| 4,696,290 | A | 9/1987 | Steffee |
| 4,743,260 | A | 5/1988 | Burton |
| 4,759,766 | A | 7/1988 | Buettner-Janz et al. |
| 4,759,769 | A | 7/1988 | Hedman et al. |
| 4,763,644 | A | 8/1988 | Webb |
| 4,772,287 | A | 9/1988 | Ray et al. |
| 4,854,311 | A | 8/1989 | Steffee |
| 4,863,476 | A | 9/1989 | Shepperd |
| 4,863,477 | A | 9/1989 | Monson |
| 4,907,577 | A | 3/1990 | Wu |
| 4,911,718 | A | 3/1990 | Lee et al. |
| 4,932,975 | A | 6/1990 | Main et al. |
| 4,946,378 | A | 8/1990 | Hirayama et al. |
| 4,946,458 | A | 8/1990 | Harms et al. |
| 5,042,982 | A | 8/1991 | Harms et al. |
| 5,047,055 | A | 9/1991 | Bao et al. |
| 5,059,194 | A | 10/1991 | Michelson |
| 5,071,437 | A | 12/1991 | Steffee |
| 5,092,867 | A | 3/1992 | Harms et al. |
| 5,108,438 | A | 4/1992 | Stone |
| 5,123,926 | A | 6/1992 | Pisharodi |
| 5,171,278 | A | 12/1992 | Pisharodi |
| 5,171,281 | A | 12/1992 | Parsons et al. |
| 5,180,393 | A | 1/1993 | Commarmond |
| 5,192,326 | A | 3/1993 | Bao et al. |
| 5,196,013 | A | 3/1993 | Harms et al. |
| 5,207,678 | A | 5/1993 | Harms et al. |
| 5,217,497 | A | 6/1993 | Mehdian |
| 5,246,458 | A | 9/1993 | Graham |
| 5,258,031 | A | 11/1993 | Salib et al. |
| 5,261,909 | A | 11/1993 | Sutterlin et al. |
| 5,306,307 | A | 4/1994 | Senter et al. |
| 5,306,309 | A | 4/1994 | Wagner et al. |
| 5,314,477 | A | 5/1994 | Marnay |
| 5,320,644 | A | 6/1994 | Baumgartner |
| 5,336,223 | A | 8/1994 | Rogers |
| 5,370,697 | A | 12/1994 | Baumgartner |
| 5,375,823 | A | 12/1994 | Navas |
| 5,397,364 | A | 3/1995 | Kozak et al. |
| 5,401,269 | A | 3/1995 | Buettner-Janz et al. |
| 5,403,315 | A | 4/1995 | Ashman |
| 5,415,661 | A | 5/1995 | Holmes |
| 5,423,816 | A | 6/1995 | Lin |
| 5,425,773 | A | 6/1995 | Boyd et al. |
| 5,443,467 | A | 8/1995 | Biedermann et al. |
| 5,458,642 | A | 10/1995 | Beer et al. |
| 5,458,643 | A | 10/1995 | Oka et al. |
| 5,480,401 | A | 1/1996 | Navas |
| 5,496,321 | A | 3/1996 | Puno et al. |
| 5,498,263 | A | 3/1996 | DiNello et al. |
| 5,507,816 | A | 4/1996 | Bullivant |
| 5,514,132 | A | 5/1996 | Csernatony et al. |
| 5,522,899 | A | 6/1996 | Michelson |
| 5,527,314 | A | 6/1996 | Brumfield et al. |
| 5,534,028 | A | 7/1996 | Bao et al. |
| 5,534,029 | A | 7/1996 | Shima |
| 5,534,030 | A | 7/1996 | Navarro et al. |
| 5,540,688 | A | 7/1996 | Navas |
| 5,545,165 | A | 8/1996 | Biedermann et al. |
| 5,514,180 | A | 9/1996 | Heggeness et al. |
| 5,556,431 | A | 9/1996 | Buttner-Janz |
| 5,562,663 | A | 10/1996 | Wisnewski et al. |
| 5,562,737 | A | 10/1996 | Graf |
| 5,562,738 | A | 10/1996 | Boyd et al. |
| 5,571,109 | A | 11/1996 | Bertagnoli |
| 5,609,635 | A | 3/1997 | Michelson |
| 5,624,442 | A | 4/1997 | Mellinger et al. |
| 5,645,599 | A | 7/1997 | Samani |
| 5,653,763 | A | 8/1997 | Errico et al. |
| 5,665,122 | A | 9/1997 | Kambin |
| 5,672,175 | A | 9/1997 | Martin |
| 5,672,176 | A | 9/1997 | Biedermann et al. |
| 5,674,294 | A | 10/1997 | Bainville et al. |
| 5,674,296 | A | 10/1997 | Bryan et al. |
| 5,676,701 | A | 10/1997 | Yuan et al. |
| 5,676,702 | A | 10/1997 | Ratron |
| 5,683,391 | A | 11/1997 | Boyd |
| 5,683,464 | A | 11/1997 | Wagner et al. |
| 5,683,465 | A | 11/1997 | Shinn et al. |
| 5,702,450 | A | 12/1997 | Bisserie |
| 5,725,527 | A | 3/1998 | Biedermann et al. |
| 5,733,284 | A | 3/1998 | Martin |
| 5,741,253 | A | 4/1998 | Michelson |
| 5,755,797 | A | 5/1998 | Baumgartner |
| 5,772,661 | A | 6/1998 | Michelson |
| 5,776,199 | A | 7/1998 | Michelson |
| 5,782,832 | A | 7/1998 | Larsen et al. |
| 5,785,647 | A | 7/1998 | Tompkins et al. |
| 5,797,909 | A | 8/1998 | Michelson |
| 5,800,549 | A | 9/1998 | Bao et al. |
| 5,800,550 | A | 9/1998 | Sertich |
| 5,810,819 | A | 9/1998 | Errico et al. |
| 5,824,093 | A | 10/1998 | Ray et al. |
| 5,824,094 | A | 10/1998 | Serhan et al. |
| 5,827,328 | A | 10/1998 | Buttermann |
| 5,860,973 | A | 1/1999 | Michelson |
| 5,861,041 | A | 1/1999 | Tienboon |
| 5,863,293 | A | 1/1999 | Richelsoph |
| 5,865,846 | A | 2/1999 | Bryan et al. |
| 5,865,848 | A | 2/1999 | Baker |
| 5,888,220 | A | 3/1999 | Felt et al. |
| 5,888,226 | A | 3/1999 | Rogozinski |
| 5,893,889 | A | 4/1999 | Harrington |
| 5,895,427 | A | 4/1999 | Kuslich et al. |
| 5,895,428 | A | 4/1999 | Berry |
| 5,899,941 | A | 5/1999 | Nishijima et al. |
| 5,928,243 | A | 7/1999 | Guyer |
| 5,935,133 | A | 8/1999 | Wagner et al. |
| 5,938,663 | A | 8/1999 | Petreto |
| 5,951,555 | A | 9/1999 | Rehak et al. |
| 5,961,518 | A | 10/1999 | Errico et al. |
| 5,961,554 | A | 10/1999 | Janson et al. |
| 5,964,769 | A | 10/1999 | Wagner et al. |
| 5,976,186 | A | 11/1999 | Bao et al. |

(56) References Cited

U.S. PATENT DOCUMENTS

| | | |
|---|---|---|
| 5,980,522 A | 11/1999 | Koros et al. |
| 5,984,967 A | 11/1999 | Zdeblick et al. |
| 5,989,250 A | 11/1999 | Wagner et al. |
| 5,989,290 A | 11/1999 | Biedermann et al. |
| 5,997,539 A | 12/1999 | Errico et al. |
| 6,001,130 A | 12/1999 | Bryan et al. |
| 6,017,344 A | 1/2000 | Errico et al. |
| 6,019,792 A | 2/2000 | Cauthen |
| 6,022,376 A | 2/2000 | Assell et al. |
| 6,030,389 A | 2/2000 | Wagner et al. |
| 6,039,763 A | 3/2000 | Shelokov |
| 6,045,552 A | 4/2000 | Zucherman et al. |
| 6,045,579 A | 4/2000 | Hochshuler et al. |
| 6,053,921 A | 4/2000 | Wagner et al. |
| 6,063,089 A | 5/2000 | Errico et al. |
| RE36,758 E | 6/2000 | Fitz |
| 6,080,193 A | 6/2000 | Hochshuler et al. |
| 6,093,205 A | 7/2000 | McLeod et al. |
| 6,096,038 A | 8/2000 | Michelson |
| 6,102,950 A | 8/2000 | Vaccaro |
| 6,106,526 A | 8/2000 | Harms et al. |
| 6,110,210 A | 8/2000 | Norton et al. |
| 6,113,637 A | 9/2000 | Gill et al. |
| 6,123,707 A | 9/2000 | Wagner et al. |
| 6,126,689 A | 10/2000 | Brett |
| 6,132,430 A | 10/2000 | Wagner et al. |
| 6,132,464 A | 10/2000 | Martin |
| 6,132,465 A | 10/2000 | Ray et al. |
| 6,136,001 A | 10/2000 | Michelson |
| 6,136,031 A | 10/2000 | Middleton |
| 6,139,579 A | 10/2000 | Steffee et al. |
| 6,146,421 A | 11/2000 | Gordon et al. |
| 6,146,422 A | 11/2000 | Lawson |
| 6,156,067 A | 12/2000 | Bryan et al. |
| 6,162,252 A | 12/2000 | Kuras et al. |
| 6,165,218 A | 12/2000 | Husson et al. |
| 6,176,882 B1 | 1/2001 | Biedermann et al. |
| 6,179,874 B1 | 1/2001 | Cauthen |
| 6,187,048 B1 | 2/2001 | Milner et al. |
| 6,200,348 B1 | 3/2001 | Biedermann et al. |
| 6,206,924 B1 | 3/2001 | Timm |
| 6,214,049 B1 | 4/2001 | Gayer et al. |
| 6,214,050 B1 | 4/2001 | Huene |
| 6,217,579 B1 | 4/2001 | Koros |
| 6,228,118 B1 | 5/2001 | Gordon |
| 6,231,609 B1 | 5/2001 | Mehdizadeh |
| 6,241,730 B1 | 6/2001 | Alby |
| 6,264,656 B1 | 7/2001 | Michelson |
| 6,290,724 B1 | 9/2001 | Marino |
| 6,296,664 B1 | 10/2001 | Middleton |
| 6,315,797 B1 | 11/2001 | Middleton |
| 6,331,179 B1 | 12/2001 | Freid et al. |
| 6,348,071 B1 | 2/2002 | Steffee et al. |
| RE37,665 E | 4/2002 | Ralph et al. |
| 6,368,350 B1 | 4/2002 | Erickson |
| 6,368,351 B1 | 4/2002 | Glenn et al. |
| 6,371,990 B1 | 4/2002 | Ferree |
| 6,375,682 B1 | 4/2002 | Fleischmann et al. |
| 6,375,683 B1 | 4/2002 | Crozet et al. |
| 6,391,030 B1 | 5/2002 | Wagner et al. |
| 6,395,032 B1 | 5/2002 | Gauchet |
| 6,395,034 B1 | 5/2002 | Suddaby |
| 6,402,784 B1 | 6/2002 | Wardlaw |
| 6,402,785 B1 | 6/2002 | Zdeblick et al. |
| 6,409,766 B1 | 6/2002 | Brett |
| 6,413,259 B1 | 7/2002 | Lyons et al. |
| 6,416,515 B1 | 7/2002 | Wagner et al. |
| 6,419,703 B1 | 7/2002 | Fallin et al. |
| 6,419,704 B1 | 7/2002 | Ferree |
| 6,436,140 B1 | 8/2002 | Liu et al. |
| 6,440,168 B1 | 8/2002 | Cauthen |
| 6,442,814 B1 | 9/2002 | Landry et al. |
| 6,443,990 B1 | 9/2002 | Aebi et al. |
| 6,447,512 B1 | 9/2002 | Landry et al. |
| 6,447,544 B1 | 9/2002 | Michelson |
| 6,447,545 B1 | 9/2002 | Bagby |
| 6,451,021 B1 | 9/2002 | Ralph et al. |
| 6,454,769 B2 | 9/2002 | Wagner et al. |
| 6,454,806 B1 | 9/2002 | Cohen et al. |
| 6,454,807 B1 | 9/2002 | Jackson |
| 6,475,218 B2 | 11/2002 | Gournay et al. |
| 6,478,822 B1 | 11/2002 | Leroux et al. |
| 6,478,823 B1 | 11/2002 | Michelson |
| 6,482,207 B1 | 11/2002 | Errico |
| 6,482,234 B1 | 11/2002 | Weber et al. |
| 6,488,710 B2 | 12/2002 | Besselink |
| 6,500,180 B1 | 12/2002 | Foley et al. |
| 6,500,205 B1 | 12/2002 | Michelson |
| 6,500,206 B1 | 12/2002 | Bryan |
| 6,520,996 B1 | 2/2003 | Manasas et al. |
| 6,524,312 B2 | 2/2003 | Landry et al. |
| 6,533,817 B1 | 3/2003 | Norton et al. |
| 6,533,818 B1 | 3/2003 | Weber et al. |
| 6,537,320 B1 | 3/2003 | Michelson |
| 6,540,748 B2 | 4/2003 | Lombardo |
| 6,558,423 B1 | 5/2003 | Michelson |
| 6,558,424 B2 | 5/2003 | Thalgott |
| 6,562,040 B1 | 5/2003 | Wagner et al. |
| 6,562,074 B2 | 5/2003 | Gerbec et al. |
| 6,565,566 B1 | 5/2003 | Wagner et al. |
| 6,565,605 B2 | 5/2003 | Goble et al. |
| 6,569,442 B2 | 5/2003 | Gan et al. |
| 6,572,653 B1 | 6/2003 | Simonson |
| 6,576,016 B1 | 6/2003 | Hochshuler et al. |
| 6,579,318 B2 | 6/2003 | Varga et al. |
| 6,579,319 B2 | 6/2003 | Goble et al. |
| 6,582,467 B1 | 6/2003 | Teitelbaum et al. |
| 6,592,624 B1 | 7/2003 | Fraser et al. |
| 6,595,992 B1 | 7/2003 | Wagner et al. |
| 6,595,998 B2 | 7/2003 | Johnson et al. |
| 6,607,530 B1 | 8/2003 | Carl et al. |
| 6,610,091 B1 | 8/2003 | Reiley |
| 6,610,094 B2 | 8/2003 | Husson |
| 6,613,050 B1 | 9/2003 | Wagner et al. |
| 6,616,671 B2 | 9/2003 | Landry et al. |
| 6,626,904 B1 | 9/2003 | Jammet et al. |
| 6,626,905 B1 | 9/2003 | Schmiel et al. |
| 6,635,062 B2 | 10/2003 | Ray et al. |
| 6,641,614 B1 | 11/2003 | Wagner et al. |
| 6,648,893 B2 | 11/2003 | Dudasik |
| 6,648,915 B2 | 11/2003 | Sazy |
| 6,648,917 B2 | 11/2003 | Gerbec et al. |
| 6,666,870 B2 | 12/2003 | Dixon |
| 6,666,891 B2 | 12/2003 | Boehm et al. |
| 6,679,915 B1 | 1/2004 | Cauthen |
| 6,682,533 B1 | 1/2004 | Dinsdale et al. |
| 6,685,742 B1 | 2/2004 | Jackson |
| 6,692,495 B1 | 2/2004 | Zacouto |
| 6,706,070 B1 | 3/2004 | Wagner et al. |
| 6,712,819 B2 | 3/2004 | Zucherman et al. |
| 6,716,247 B2 | 4/2004 | Michelson |
| 6,719,796 B2 | 4/2004 | Cohen et al. |
| 6,733,531 B1 | 5/2004 | Trieu |
| 6,736,850 B2 | 5/2004 | Davis |
| 6,743,257 B2 | 6/2004 | Castro |
| 6,758,861 B2 | 7/2004 | Ralph et al. |
| 6,773,460 B2 | 8/2004 | Jackson |
| 6,802,844 B2 | 10/2004 | Ferree |
| 6,811,567 B2 | 11/2004 | Reiley |
| 6,821,298 B1 | 11/2004 | Jackson |
| 6,852,129 B2 | 2/2005 | Gerbec et al. |
| 6,863,673 B2 | 3/2005 | Gerbec et al. |
| 6,893,464 B2 | 5/2005 | Kiester |
| 6,896,680 B2 | 5/2005 | Michelson |
| 6,902,580 B2 | 6/2005 | Fallin et al. |
| 6,928,284 B2 | 8/2005 | Palat et al. |
| 6,936,070 B1 | 8/2005 | Muhanna |
| 6,936,071 B1 | 8/2005 | Marnay et al. |
| 6,953,477 B2 | 10/2005 | Berry |
| 6,962,606 B2 | 11/2005 | Michelson |
| 6,964,664 B2 | 11/2005 | Freid et al. |
| 6,966,929 B2 | 11/2005 | Mitchell |
| 6,966,930 B2 | 11/2005 | Arnin et al. |
| 6,974,478 B2 | 12/2005 | Reiley et al. |

(56) References Cited

U.S. PATENT DOCUMENTS

| | | |
|---|---|---|
| 6,981,989 B1 | 1/2006 | Fleischmann et al. |
| 6,991,632 B2 | 1/2006 | Ritland |
| 6,994,727 B2 | 2/2006 | Khandkar et al. |
| 6,997,929 B2 | 2/2006 | Manzi et al. |
| 7,011,685 B2 | 3/2006 | Arnin et al. |
| 7,018,415 B1 | 3/2006 | McKay |
| 7,029,475 B2 | 4/2006 | Panjabi |
| 7,060,073 B2 | 6/2006 | Frey et al. |
| 7,083,622 B2 | 8/2006 | Simonson |
| 7,083,649 B2 | 8/2006 | Zucherman et al. |
| 7,090,698 B2 | 8/2006 | Goble et al. |
| 7,101,398 B2 | 9/2006 | Dooris et al. |
| 7,118,579 B2 | 10/2006 | Michelson |
| 7,118,580 B1 | 10/2006 | Beyersdorff et al. |
| 7,128,760 B2 | 10/2006 | Michelson |
| 7,147,664 B2 | 12/2006 | Louis et al. |
| 7,153,310 B2 | 12/2006 | Ralph et al. |
| 7,198,644 B2 | 4/2007 | Schultz et al. |
| 7,204,852 B2 | 4/2007 | Marnay et al. |
| 7,204,853 B2 | 4/2007 | Gordon et al. |
| 7,270,681 B2 | 9/2007 | Cauthen |
| 7,273,496 B2 | 9/2007 | Mitchell |
| 7,291,150 B2 | 11/2007 | Graf |
| 7,291,173 B2 | 11/2007 | Richelsoph et al. |
| 7,311,713 B2 | 12/2007 | Johnson et al. |
| 7,316,714 B2 | 1/2008 | Gordon et al. |
| 7,318,839 B2 | 1/2008 | Malberg et al. |
| 7,320,707 B2 | 1/2008 | Zucherman |
| 7,326,250 B2 | 2/2008 | Beaurain et al. |
| 7,338,525 B2 | 3/2008 | Ferree |
| 7,338,527 B2 | 3/2008 | Blatt et al. |
| 7,364,589 B2 | 4/2008 | Eisermann |
| 7,473,276 B2 | 1/2009 | Aebi et al. |
| 7,476,238 B2 | 1/2009 | Panjabi |
| 7,485,146 B1 | 2/2009 | Crook et al. |
| 7,517,359 B2 | 4/2009 | Drewry et al. |
| 7,547,309 B2 | 6/2009 | Bertagnoli et al. |
| 7,550,009 B2 | 6/2009 | Arnin et al. |
| 7,556,651 B2 | 7/2009 | Humphreys et al. |
| 7,615,068 B2 | 11/2009 | Timm et al. |
| 7,635,379 B2 | 12/2009 | Callahan et al. |
| 7,682,396 B2 | 3/2010 | Beaurain et al. |
| 7,699,875 B2 | 4/2010 | Timm et al. |
| 7,708,778 B2 | 5/2010 | Gordon et al. |
| 7,713,287 B2 | 5/2010 | Timm et al. |
| 7,713,288 B2 | 5/2010 | Timm et al. |
| 7,753,958 B2 | 7/2010 | Gordon et al. |
| 7,771,479 B2 | 8/2010 | Humphreys et al. |
| 7,785,351 B2 | 8/2010 | Gordon et al. |
| 7,794,480 B2 | 9/2010 | Gordon et al. |
| 7,799,082 B2 | 9/2010 | Gordon et al. |
| 7,811,309 B2 | 10/2010 | Timm et al. |
| 7,819,801 B2 | 10/2010 | Miles et al. |
| 7,909,869 B2 | 3/2011 | Gordon et al. |
| 7,909,877 B2 | 3/2011 | Krueger et al. |
| 7,931,675 B2 | 4/2011 | Panjabi et al. |
| 7,942,905 B2 | 5/2011 | Lim et al. |
| 7,951,170 B2 | 5/2011 | Jackson |
| 7,959,677 B2 | 6/2011 | Landry et al. |
| 8,016,829 B2 * | 9/2011 | Mahoney et al. ............ 606/86 A |
| 8,025,684 B2 * | 9/2011 | Garcia-Bengochea et al. ................. 606/279 |
| 8,043,379 B2 | 10/2011 | Moumene et al. |
| 8,052,723 B2 | 11/2011 | Gordon et al. |
| 8,057,548 B2 * | 11/2011 | Abernathie et al. ....... 623/17.16 |
| 8,062,375 B2 | 11/2011 | Glerum et al. |
| 8,105,382 B2 | 1/2012 | Olmos et al. |
| 8,118,869 B2 | 2/2012 | Gordon et al. |
| 8,118,870 B2 | 2/2012 | Gordon et al. |
| 8,118,871 B2 | 2/2012 | Gordon et al. |
| 8,118,872 B2 * | 2/2012 | Trudeau et al. ............ 623/17.16 |
| 8,123,810 B2 | 2/2012 | Gordon et al. |
| 8,147,550 B2 | 4/2012 | Gordon et al. |
| 8,157,844 B2 | 4/2012 | Gimbel et al. |
| 8,162,994 B2 | 4/2012 | Gimbel et al. |
| 8,172,903 B2 | 5/2012 | Gordon et al. |
| 8,182,514 B2 | 5/2012 | Gimbel et al. |
| 8,187,330 B2 | 5/2012 | Gimbel et al. |
| 8,257,440 B2 | 9/2012 | Gordon et al. |
| 8,267,965 B2 | 9/2012 | Gimbel et al. |
| 8,377,098 B2 | 2/2013 | Landry et al. |
| 8,388,687 B2 | 3/2013 | Gimbel et al. |
| 8,523,912 B2 | 9/2013 | Gimbel et al. |
| 8,597,358 B2 | 12/2013 | Landry et al. |
| 8,603,168 B2 | 12/2013 | Gordon et al. |
| 8,647,386 B2 | 2/2014 | Gordon et al. |
| 8,753,398 B2 | 6/2014 | Gordon et al. |
| 2001/0020476 A1 | 9/2001 | Gan et al. |
| 2001/0032020 A1 | 10/2001 | Besselink |
| 2002/0040243 A1 | 4/2002 | Attali et al. |
| 2002/0045945 A1 | 4/2002 | Liu et al. |
| 2002/0065557 A1 | 5/2002 | Goble et al. |
| 2002/0068977 A1 | 6/2002 | Jackson |
| 2002/0072801 A1 | 6/2002 | Michelson |
| 2002/0082701 A1 | 6/2002 | Zdeblick et al. |
| 2002/0091390 A1 | 7/2002 | Michelson |
| 2002/0095154 A1 | 7/2002 | Atkinson et al. |
| 2002/0123806 A1 | 9/2002 | Reiley |
| 2002/0128659 A1 | 9/2002 | Michelson |
| 2002/0128714 A1 | 9/2002 | Manasas et al. |
| 2002/0130112 A1 | 9/2002 | Manasas et al. |
| 2002/0138077 A1 | 9/2002 | Ferree |
| 2002/0143401 A1 | 10/2002 | Michelson |
| 2003/0028250 A1 | 2/2003 | Reiley et al. |
| 2003/0040802 A1 | 2/2003 | Errico |
| 2003/0055427 A1 | 3/2003 | Graf |
| 2003/0069643 A1 | 4/2003 | Ralph et al. |
| 2003/0074063 A1 | 4/2003 | Gerbec et al. |
| 2003/0074066 A1 | 4/2003 | Errico et al. |
| 2003/0074067 A1 | 4/2003 | Errico et al. |
| 2003/0074068 A1 | 4/2003 | Errico et al. |
| 2003/0074069 A1 | 4/2003 | Errico et al. |
| 2003/0074070 A1 | 4/2003 | Errico et al. |
| 2003/0074071 A1 | 4/2003 | Errico et al. |
| 2003/0074072 A1 | 4/2003 | Errico et al. |
| 2003/0074073 A1 | 4/2003 | Errico et al. |
| 2003/0074074 A1 | 4/2003 | Errico et al. |
| 2003/0135275 A1 | 7/2003 | Garcia et al. |
| 2003/0135277 A1 | 7/2003 | Bryan et al. |
| 2003/0139812 A1 | 7/2003 | Gacia et al. |
| 2003/0149483 A1 | 8/2003 | Michelson |
| 2003/0176923 A1 | 9/2003 | Keller et al. |
| 2003/0191470 A1 | 10/2003 | Ritland |
| 2003/0204259 A1 | 10/2003 | Goble et al. |
| 2003/0204260 A1 | 10/2003 | Ferree |
| 2003/0220643 A1 | 11/2003 | Ferree |
| 2003/0225409 A1 | 12/2003 | Freid et al. |
| 2003/0233145 A1 | 12/2003 | Landry et al. |
| 2004/0006391 A1 | 1/2004 | Reiley |
| 2004/0019353 A1 | 1/2004 | Freid et al. |
| 2004/0030387 A1 | 2/2004 | Landry et al. |
| 2004/0030389 A1 | 2/2004 | Ferree |
| 2004/0039448 A1 | 2/2004 | Pisharodi |
| 2004/0044411 A1 | 3/2004 | Suddaby |
| 2004/0049190 A1 | 3/2004 | Biedermann et al. |
| 2004/0049271 A1 | 3/2004 | Biedermann et al. |
| 2004/0049272 A1 | 3/2004 | Reiley |
| 2004/0049273 A1 | 3/2004 | Reiley |
| 2004/0049274 A1 | 3/2004 | Reiley |
| 2004/0049275 A1 | 3/2004 | Reiley |
| 2004/0049276 A1 | 3/2004 | Reiley |
| 2004/0049277 A1 | 3/2004 | Reiley |
| 2004/0049278 A1 | 3/2004 | Reiley |
| 2004/0049280 A1 | 3/2004 | Cauthen |
| 2004/0049281 A1 | 3/2004 | Reiley |
| 2004/0087947 A1 | 5/2004 | Lim et al. |
| 2004/0093083 A1 | 5/2004 | Branch et al. |
| 2004/0102774 A1 | 5/2004 | Trieu |
| 2004/0106997 A1 | 6/2004 | Lieberson |
| 2004/0117020 A1 | 6/2004 | Frey et al. |
| 2004/0127989 A1 | 7/2004 | Dooris et al. |
| 2004/0133278 A1 | 7/2004 | Marino et al. |
| 2004/0133281 A1 | 7/2004 | Khandkar et al. |
| 2004/0138662 A1 | 7/2004 | Landry et al. |

(56) References Cited

U.S. PATENT DOCUMENTS

| | | |
|---|---|---|
| 2004/0138749 A1 | 7/2004 | Zucherman |
| 2004/0143265 A1 | 7/2004 | Landry et al. |
| 2004/0143332 A1 | 7/2004 | Krueger et al. |
| 2004/0147928 A1 | 7/2004 | Landry et al. |
| 2004/0153065 A1 | 8/2004 | Lim |
| 2004/0167626 A1 | 8/2004 | Geremakis et al. |
| 2004/0181223 A1 | 9/2004 | Ritland |
| 2004/0181284 A1 | 9/2004 | Simonson |
| 2004/0220567 A1 | 11/2004 | Eisermann et al. |
| 2004/0236327 A1 | 11/2004 | Paul et al. |
| 2004/0236329 A1 | 11/2004 | Panjabi |
| 2004/0243240 A1 | 12/2004 | Beaurain et al. |
| 2004/0254643 A1 | 12/2004 | Jackson |
| 2004/0254644 A1 | 12/2004 | Taylor |
| 2004/0267364 A1 | 12/2004 | Carli et al. |
| 2004/0267369 A1 | 12/2004 | Lyons et al. |
| 2005/0010295 A1 | 1/2005 | Michelson |
| 2005/0015146 A1 | 1/2005 | Louis et al. |
| 2005/0015149 A1 | 1/2005 | Michelson |
| 2005/0021144 A1 | 1/2005 | Malberg et al. |
| 2005/0027361 A1 | 2/2005 | Reiley |
| 2005/0033431 A1 | 2/2005 | Gordon et al. |
| 2005/0033432 A1 | 2/2005 | Gordon et al. |
| 2005/0033437 A1 | 2/2005 | Bao et al. |
| 2005/0033439 A1 | 2/2005 | Gordon et al. |
| 2005/0060034 A1 | 3/2005 | Berry |
| 2005/0085815 A1 | 4/2005 | Harms et al. |
| 2005/0107881 A1 | 5/2005 | Alleyne et al. |
| 2005/0113927 A1 | 5/2005 | Malek |
| 2005/0124991 A1 | 6/2005 | Jahng |
| 2005/0125061 A1 | 6/2005 | Zucherman et al. |
| 2005/0131406 A1 | 6/2005 | Reiley |
| 2005/0143818 A1 | 6/2005 | Yuan et al. |
| 2005/0149020 A1 | 7/2005 | Jahng |
| 2005/0149023 A1 | 7/2005 | Ritland |
| 2005/0154461 A1 | 7/2005 | Humphreys et al. |
| 2005/0154465 A1 | 7/2005 | Hodges et al. |
| 2005/0154466 A1 | 7/2005 | Humphreys et al. |
| 2005/0159818 A1 | 7/2005 | Blain |
| 2005/0171543 A1 | 8/2005 | Timm et al. |
| 2005/0171608 A1 | 8/2005 | Peterman et al. |
| 2005/0171610 A1 | 8/2005 | Humphreys et al. |
| 2005/0177156 A1 | 8/2005 | Timm et al. |
| 2005/0177157 A1 | 8/2005 | Jahng |
| 2005/0177164 A1 | 8/2005 | Walters et al. |
| 2005/0177166 A1 | 8/2005 | Timm et al. |
| 2005/0182401 A1 | 8/2005 | Timm et al. |
| 2005/0182409 A1 | 8/2005 | Callahan et al. |
| 2005/0203517 A1 | 9/2005 | Jahng et al. |
| 2005/0209697 A1 | 9/2005 | Paponneau et al. |
| 2005/0209698 A1 | 9/2005 | Gordon et al. |
| 2005/0222569 A1 | 10/2005 | Panjabi |
| 2005/0228500 A1 | 10/2005 | Kim et al. |
| 2005/0245930 A1 | 11/2005 | Timm et al. |
| 2005/0256578 A1 | 11/2005 | Blatt et al. |
| 2005/0117725 A1 | 12/2005 | Parson |
| 2005/0273167 A1 | 12/2005 | Triplett et al. |
| 2005/0273171 A1 | 12/2005 | Gordon et al. |
| 2005/0273173 A1 | 12/2005 | Gordon et al. |
| 2005/0273174 A1 | 12/2005 | Gordon et al. |
| 2005/0273175 A1 | 12/2005 | Gordon et al. |
| 2005/0278026 A1 | 12/2005 | Gordon et al. |
| 2005/0283244 A1 | 12/2005 | Gordon et al. |
| 2005/0283245 A1 | 12/2005 | Gordon et al. |
| 2005/0283247 A1 | 12/2005 | Gordon et al. |
| 2005/0283248 A1 | 12/2005 | Gordon et al. |
| 2005/0288670 A1 | 12/2005 | Panjabi et al. |
| 2006/0009768 A1 | 1/2006 | Ritland |
| 2006/0009850 A1 | 1/2006 | Frigg et al. |
| 2006/0015100 A1 | 1/2006 | Panjabi et al. |
| 2006/0036240 A1 | 2/2006 | Colleran |
| 2006/0036245 A1 | 2/2006 | Stern |
| 2006/0084986 A1 | 4/2006 | Grinberg et al. |
| 2006/0089717 A1 | 4/2006 | Krishna et al. |
| 2006/0095132 A1 | 5/2006 | Kirschman |
| 2006/0129244 A1 | 6/2006 | Ensign |
| 2006/0142759 A1 | 6/2006 | Arnin et al. |
| 2006/0149228 A1 | 7/2006 | Schlapfer et al. |
| 2006/0149229 A1 | 7/2006 | Kwak et al. |
| 2006/0149278 A1 | 7/2006 | Abdou |
| 2006/0149383 A1 | 7/2006 | Arnin et al. |
| 2006/0155377 A1 | 7/2006 | Beaurain et al. |
| 2006/0167547 A1 | 7/2006 | Suddaby |
| 2006/0189983 A1 | 8/2006 | Fallin et al. |
| 2006/0195114 A1 | 8/2006 | Bertagnoli |
| 2006/0195191 A1 | 8/2006 | Sweeney et al. |
| 2006/0195192 A1 | 8/2006 | Gordon et al. |
| 2006/0217712 A1 | 9/2006 | Mueller et al. |
| 2006/0229729 A1 | 10/2006 | Gordon |
| 2006/0241642 A1 | 10/2006 | Arnin et al. |
| 2006/0241769 A1 | 10/2006 | Gordon et al. |
| 2006/0241770 A1 | 10/2006 | Rhoda et al. |
| 2006/0241771 A1 | 10/2006 | Gordon et al. |
| 2006/0247635 A1 | 11/2006 | Gordon et al. |
| 2006/0247779 A1 | 11/2006 | Gordon et al. |
| 2006/0260483 A1 | 11/2006 | Hartmann et al. |
| 2006/0264937 A1 | 11/2006 | White |
| 2006/0265068 A1 | 11/2006 | Schwab |
| 2006/0265074 A1 | 11/2006 | Krishna |
| 2007/0010886 A1 | 1/2007 | Banick |
| 2007/0073405 A1 | 3/2007 | Verhulst et al. |
| 2007/0073406 A1 | 3/2007 | Gordon et al. |
| 2007/0093828 A1 | 4/2007 | Abdou |
| 2007/0093846 A1 | 4/2007 | Frigg et al. |
| 2007/0162137 A1 | 7/2007 | Kloss et al. |
| 2007/0213720 A1 | 9/2007 | Gordon et al. |
| 2007/0213821 A1 | 9/2007 | Kwak et al. |
| 2007/0225814 A1 | 9/2007 | Atkinson |
| 2007/0239279 A1 | 10/2007 | Francis |
| 2007/0270814 A1 | 11/2007 | Lim et al. |
| 2007/0270838 A1 | 11/2007 | Bruneau et al. |
| 2007/0270972 A1 | 11/2007 | Gordon et al. |
| 2007/0288094 A1 | 12/2007 | Krishna et al. |
| 2008/0015702 A1 | 1/2008 | Lakin et al. |
| 2008/0021285 A1 | 1/2008 | Drzyzga et al. |
| 2008/0027547 A1 | 1/2008 | Yu et al. |
| 2008/0033562 A1 | 2/2008 | Krishna |
| 2008/0065079 A1 | 3/2008 | Bruneau et al. |
| 2008/0133013 A1 | 6/2008 | Duggal et al. |
| 2008/0161853 A1 | 7/2008 | Arnold et al. |
| 2008/0177310 A1 | 7/2008 | Reiley |
| 2008/0183204 A1 | 7/2008 | Greenhalgh et al. |
| 2008/0234732 A1 | 9/2008 | Landry et al. |
| 2008/0234740 A1 | 9/2008 | Landry et al. |
| 2008/0234741 A1 | 9/2008 | Landry et al. |
| 2008/0234764 A1 | 9/2008 | Landry et al. |
| 2008/0234823 A1 | 9/2008 | Landry et al. |
| 2008/0300685 A1 | 12/2008 | Carls et al. |
| 2008/0312692 A1 | 12/2008 | Brennan et al. |
| 2009/0005817 A1 | 1/2009 | Friedrich et al. |
| 2009/0076549 A1 | 3/2009 | Lim et al. |
| 2009/0093846 A1 | 4/2009 | Hestad |
| 2009/0105757 A1 | 4/2009 | Gimbel et al. |
| 2009/0105758 A1 | 4/2009 | Gimbel et al. |
| 2009/0105759 A1 | 4/2009 | Gimbel et al. |
| 2009/0105764 A1 | 4/2009 | Jackson |
| 2009/0105820 A1 | 4/2009 | Jackson |
| 2009/0105827 A1 | 4/2009 | Gimbel et al. |
| 2009/0105828 A1 | 4/2009 | Gimbel et al. |
| 2009/0105829 A1 | 4/2009 | Gimbel et al. |
| 2009/0138091 A1* | 5/2009 | Ray .................. 623/17.16 |
| 2009/0143862 A1 | 6/2009 | Trieu |
| 2009/0177196 A1 | 7/2009 | Zlock et al. |
| 2009/0270870 A1 | 10/2009 | Zubok et al. |
| 2010/0082109 A1 | 4/2010 | Greenhalgh et al. |
| 2010/0174317 A1 | 7/2010 | Timm et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222819 A1 | 9/2010 | Timm et al. |
| 2010/0222884 A1 | 9/2010 | Greenhalgh |
| 2010/0292796 A1 | 11/2010 | Greenhalgh et al. |
| 2010/0298941 A1 | 11/2010 | Hes et al. |
| 2010/0331985 A1 | 12/2010 | Gordon et al. |

(56) References Cited

U.S. PATENT DOCUMENTS

| | | | |
|---|---|---|---|
| 2011/0196428 | A1 | 8/2011 | Panjabi et al. |
| 2012/0143254 | A1 | 6/2012 | Gimbel et al. |
| 2012/0245689 | A1 | 9/2012 | Gimbel et al. |
| 2012/0310349 | A1 | 12/2012 | Gordon et al. |
| 2013/0245769 | A1 | 9/2013 | Gimbel et al. |

FOREIGN PATENT DOCUMENTS

| | | |
|---|---|---|
| WO | 2006119447 | 11/2006 |
| WO | 2012134980 | 10/2012 |

OTHER PUBLICATIONS

U. S. P.T. O. Non-Final Office Action for U.S. Appl. No. 11/655,723, mailed May 20, 2014.
Co-pending U.S. Appl. No. 14/185,561 entitled "Expandable Fusion Device for Positioning Between Adjacent Vertebral Bodies" to Wagner, filed Feb. 20, 2014.
E.P.O. Decision to Grant for European Application No. 07 758 171.8 mailed on May 30, 2014.
U. S. P.T. O. Advisory Action for U.S. Appl. No. 11/134,055, mailed Jul. 8, 2013.
U. S. P.T. O. Final Office Action for U.S. Appl. No. 13/306,535, mailed Jul. 18, 2013.
U. S. P.T. O. Advisory Action for U.S. Appl. No. 13/306,535, mailed Sep. 9, 2013.
Co-pending U.S. Appl. No. 13/967,776 entitled "Expandable Intervertebral Implant" to Gordon et al., filed Aug. 15, 2013.
E.P. Communication Pursuant to Article 94(3) EPC for Application No. 08713804.6-2310 mailed Dec. 5, 2013.
International Preliminary Report on Patentability for International Application No. PCT/US2012/030248 mailed Oct. 23, 2012, 11 pages.
U. S. P.T. O. Non-Final Office Action for U.S. Appl. No. 11/655,737, mailed Mar. 15, 2013.
U. S. P.T. O. Notice of Allowance for U.S. Appl. No. 11/975,916, mailed Jan. 28, 2013.
Co-pending U.S. Appl. No. 13/784,224 entitled "Interbody Device Insertion Systems and Methods" to Gimbel et al., filed Mar. 4, 2013.
E.P. Communication Pursuant to Article 94(3) EPC for Application No. 08713804.6-2310 mailed Jan. 22, 2013.
J.P. Notice of Reason for Refusal for Japanese Application No. 2009-546510 mailed on Oct. 9, 2012.
U. S. P.T. O. Final Office Action for U.S. Appl. No. 11/134,055, mailed Apr. 18, 2013.
E.P.O. Communication Pursuant to Article 94(3) for European Application No. 07 758 171.8 mailed on Feb. 26, 2013.

* cited by examiner

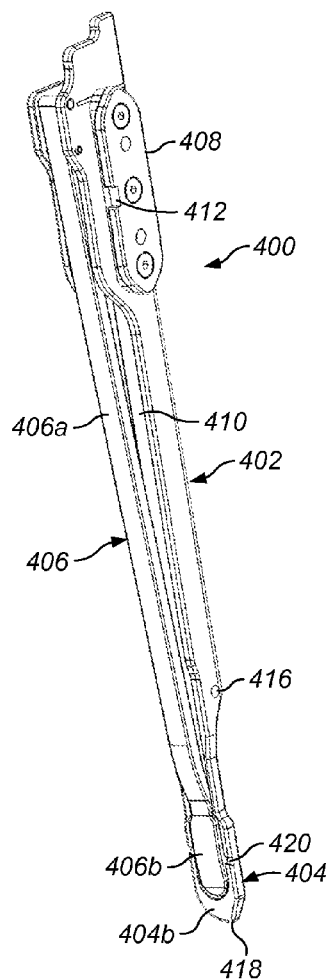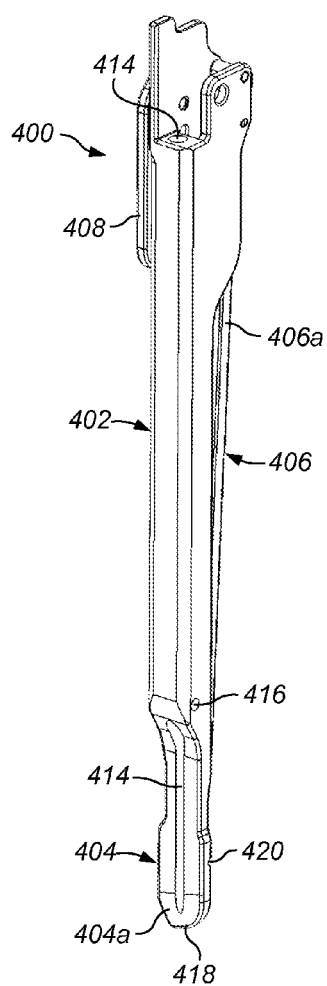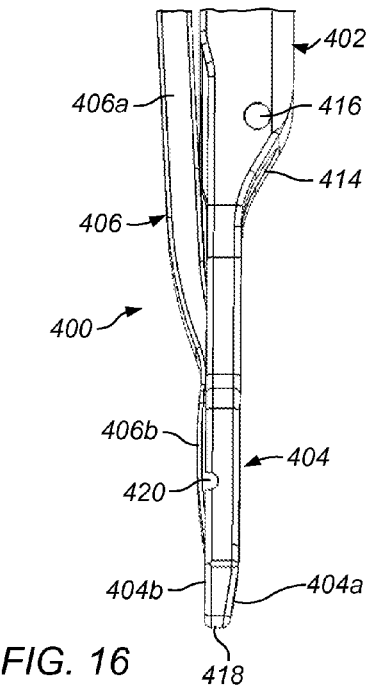
FIG. 14
FIG. 15
FIG. 16

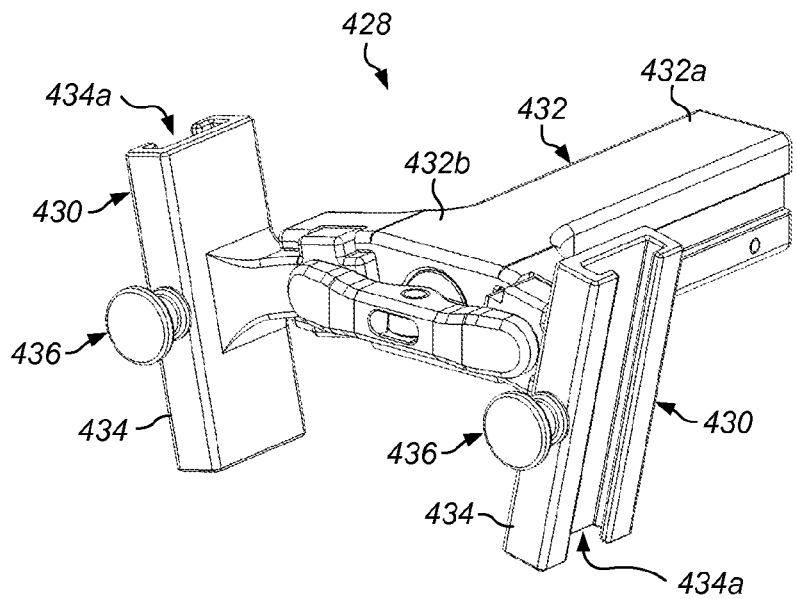
FIG. 19
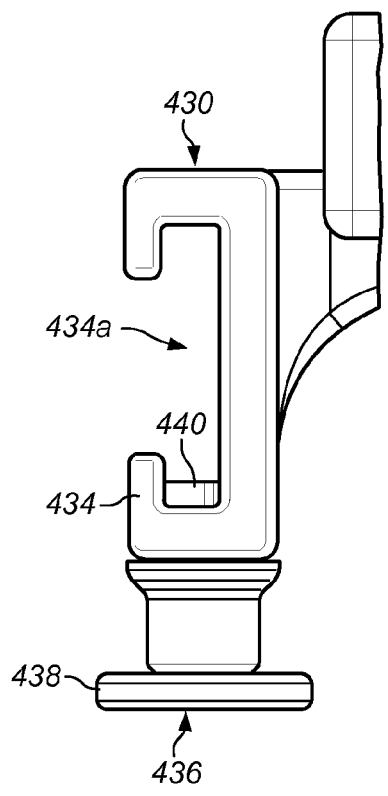 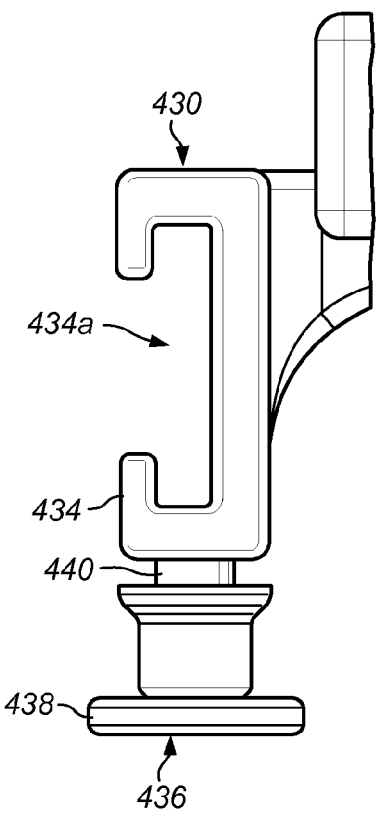
FIG. 20   FIG. 21

INTERBODY DEVICE INSERTION SYSTEMS AND METHODS

PRIORITY CLAIM

This application is a continuation of U.S. patent application Ser. No. 13/072,511 entitled "INTERBODY DEVICE INSERTION SYSTEMS AND METHODS" filed on Mar. 25, 2011, which is incorporated by reference herein.

BACKGROUND

1. Field of the Invention

Embodiments of the invention generally relate to functional spinal implant assemblies for insertion into an intervertebral space between adjacent vertebrae of a human spine. More specifically, embodiments relate to methods of using and installing interbody devices.

2. Description of Related Art

The human spine is a complex mechanical structure including alternating bony vertebrae and fibrocartilaginous discs that are connected by strong ligaments and supported by musculature that extends from the skull to the pelvis and provides axial support to the body. The intervertebral discs provide mechanical cushion between adjacent vertebral segments of the spinal column and generally include two basic components: the nucleus pulposus and the annulus fibrosis. The intervertebral discs are positioned between two vertebral end plates. The annulus fibrosis forms the perimeter of the disc and is a tough outer ring that binds adjacent vertebrae together. The end plates are made of thin cartilage overlying a thin layer of hard cortical bone that attaches to the spongy, cancellous bone of a vertebra. The vertebrae generally include a vertebral foramen bounded by the anterior vertebral body and the neural arch, which consists of two pedicles that are united posteriorly by the laminae. The spinous and transverse processes protrude from the neural arch. The superior and inferior articular facets lie at the root of the transverse process.

The spine is a flexible structure capable of a high degree of curvature and twist in nearly every direction. The motion segment or functional spinal unit (FSU) is the basic motion unit of the lumbar spine. The anterior elements of the FSU include the vertebral bodies, the intervertebral disc, and the connecting soft tissues and ligaments. The posterior elements of the FSU include the bony ring created by the pedicles and lamina, the facet joints, and the connecting soft tissues and ligaments. The facet joints are located on both sides at the junction of superior and inferior bony projections of the posterior elements.

The total motion of the spine results from the cumulative motion of the individual FSUs. Each motion segment allows rotational motion in three directions (flexion-extension, lateral bending, and axial rotation) and translational motion in three directions (anterior-posterior, medial-lateral, and superior-inferior). The available motion is primarily governed by the intervertebral disc, facet joints, and ligaments. Typical maximum amounts of lumbar rotation are up to about 17° of flexion-extension, 6° of lateral bending, and 3° of axial rotation. Moderate motions of the spine during everyday living may result in less than 10° of flexion-extension.

Translation of one vertebral body with respect to an adjacent vertebral body can be up to a few millimeters during rotation. The quality of the motion is described by the shape of the motion segment moment-rotation curve. The motion segment moment-rotation curve is the rotational response of the FSU due to loading away from the center of rotation. The moment-rotation curves are non-linear with an initial low stiffness region, followed by a higher stiffness region. The initial region of high flexibility, where spinal motion is produced with less resistance to bending moments, is typically referred to as the neutral zone. Typically, the neutral zone ranges from 10-50% of the total range of motion. The stiffness (Nm/deg) in the neutral zone is about 10-30% of the high stiffness region. Alterations to the FSU caused by surgical intervention, degeneration, acute injury, or other factors are thought to change this non-linear behavior.

Genetic or developmental irregularities, trauma, chronic stress, and degenerative wear can result in spinal pathologies for which surgical intervention may be necessary. In cases of deterioration, disease, or injury, an intervertebral disc, or a portion of the intervertebral disc, may be removed from the human spine during a discectomy.

After some discectomies, one or more non-dynamic intervertebral devices may be placed in the disc space to fuse or promote fusion of the adjacent vertebrae. During some procedures, fusion may be combined with posterior fixation to address intervertebral disc and/or facet problems. The fusion procedure (e.g., posterior lumbar interbody fusion) and the posterior fixation procedure may be performed using a posterior approach. The posterior fixation and non-dynamic intervertebral devices may cooperate to inhibit motion and promote bone healing. Fusing two vertebrae together results in some loss of motion. Fusing two vertebrae together may also result in the placement of additional stress on one or more adjacent functional spinal units. The additional stress may cause deterioration of an adjacent functional spinal unit that may result in the need for an additional surgical procedure or procedures.

After some discectomies, a dynamic intervertebral device (DID) may be placed in the disc space. The DID may allow for movement of adjacent vertebrae coupled to the DID relative to each other. U.S. Pat. No. 4,863,477 to Monson, which is incorporated herein by reference, discloses a resilient dynamic device intended to replace the resilience of a natural human spinal disc. U.S. Pat. No. 5,192,326 to Bao et al., which is incorporated herein by reference, describes a prosthetic nucleus for replacing just the nucleus portion of a human spinal disc. U.S. Patent Application Publication No. 2005/0021144 to Malberg et al., which is incorporated herein by reference, describes an expandable spinal implant. Allowing for movement of the vertebrae coupled to the disc prosthesis may promote the distribution of stress that reduces or eliminates the deterioration of adjacent functional spinal units.

An intervertebral device may be positioned between vertebrae using a posterior approach, an anterior approach, a lateral approach, or other type of approach. A challenge of positioning a device between adjacent vertebrae using a posterior approach is that a device large enough to contact the end plates and slightly expand the space must be inserted through a limited space. This challenge is often further heightened by the presence of posterior osteophytes, which may cause "fish mouthing" of the posterior vertebral end plates and result in very limited access to the disc. A further challenge in degenerative disc spaces is the tendency of the disc space to assume a lenticular shape, which may require a larger implant than can be easily introduced without causing trauma to adjacent nerve roots. The size of rigid devices that may safely be introduced into the disc space is thereby limited. During some spinal fusion procedures using a posterior approach, two implants are inserted between the vertebrae. During some posterior procedures, one or both facet joints between the vertebrae may be removed to provide additional room for the insertion of a fusion device. Removal of the facet may also allow for the removal of soft tissue surrounding the facet (for example, the facet capsule) that work to resist posterior distraction.

The anterior approach poses significant challenges as well. Though the surgeon may gain very wide access to the interbody space from the anterior approach, this approach has its own set of complications and limitations. The retroperitoneal approach usually requires the assistance of a surgeon skilled in dealing with the visceral contents and the great vessels. The spine surgeon has limited access to the nerve roots and little or no ability to access or replace the facet joints. Complications of the anterior approach that are approach specific include retrograde ejaculation, ureteral injury, and great vessel injury. Injury to the great vessels may result in massive blood loss, postoperative venous stasis, limb loss, or death. The anterior approach is often more difficult in patients with significant obesity and may be virtually impossible in the face of previous retroperitoneal surgery.

Despite the difficulties of the anterior approach, the anterior approach does allow for the wide exposure needed to place a large device. In accessing the spine anteriorly, one of the major structural ligaments, the anterior longitudinal ligament, must be completely divided. A large amount of anterior annulus must also be removed along with the entire nucleus. Once these structures have been resected, the vertebral bodies may need to be over distracted to place the device within the disc space and restore disc space height. Failure to adequately tension the posterior annulus and ligaments increases the risk of device failure and/or migration. Yet in the process of placing these devices, the ligaments are overstretched while the devices are forced into the disc space under tension. Over distraction can damage the ligaments and the nerve roots. The anterior disc replacement devices currently available or in clinical trials may be too large to be placed posteriorly, and may require over distraction during insertion to allow the ligaments to hold them in position.

A facet joint or facet joints of a functional spinal unit may be subjected to deterioration, disease or trauma that requires surgical intervention. Disc degeneration is often coupled with facet degeneration, so that disc replacement only may not be sufficient treatment for a large group of patients.

Facet degeneration may be addressed using a posterior approach. Thus a second surgical approach may be required if the disc degeneration is treated using an anterior approach. The need to address facet degeneration has led to the development of facet replacement devices. Some facet replacement devices are shown in U.S. Pat. No. 6,419,703 to Fallin et al.; U.S. Pat. No. 6,902,580 to Fallin et al.; U.S. Pat. No. 6,610,091 to Reiley; U.S. Pat. No. 6,811,567 to Reiley; and U.S. Pat. No. 6,974,478 to Reiley et al, each of which is incorporated herein by reference. The facet replacement devices may be used in conjunction with anterior disc replacement devices, but the facet replacement devices are usually not designed to provide a common center of rotation with the anterior disc replacement devices. The use of an anterior disc replacement device that has a fixed center of rotation contrary to the fixed center of rotation of the facet replacement device may restrict or diminish motion and be counterproductive to the intent of the operation.

During some spinal stabilization procedures a posterior fixation system may be coupled to the spine. During some procedures, posterior fixation systems may be coupled to each side of the spine. The posterior fixation systems may include elongated members that are coupled to vertebrae by fasteners (e.g., hooks and screws). One or more transverse connectors may be connected to the posterior fixation systems to join and stabilize the posterior fixation systems.

During some spinal stabilization procedures, dynamic posterior stabilization systems may be used. U.S. Patent Publication Nos. 2005/0182409 to Callahan et al.; 2005/0245930 to Timm et al.; and 2006/0009768 to Ritland, each of which is incorporated herein by reference, disclose dynamic posterior stabilization systems.

During some spinal stabilization procedures, a dynamic interbody device or devices may be used in conjunction with one or more dynamic posterior stabilization systems. U.S. Patent Publication No. 2006/0247779 to Gordon et al., U.S. Patent Publication No. 2008/0234740 to Landry et al., and U.S. Patent Publication No. 2009/0105829 to Gimbel et al. each of which is incorporated herein by reference, disclose dynamic interbody devices and dynamic posterior stabilization systems that may be used together to stabilize a portion of a spine.

Unfortunately, in the above described techniques, it may be difficult to prepare an intevertabral disc space for receipt of one or more spinal implants and it may also be difficult to accurately place the implants and devices described above within the disc space. For example, when placing a dynamic interbody device into the disc space it may be required that the device is positioned precisely relative to the adjacent vertebra to provide for effective operation of the implant devices during use. Moreover, in some instances where multiple dynamic interbody devices are placed within the disc space, it may be required that the devices are positioned precisely relative to one another to provide for effective operation of the implant devices during use. Furthermore, improper placement of devices may increase the risk of injury to the patient, including nerve root damage during disc space preparation and interbody device placement.

SUMMARY

Various embodiments of interbody devices and insertion methods for installing interbody devices are described. In some embodiments, provided is a method of implanting an interbody device into a disc space located between a first and second vertebra including inserting a base plate of a first implant trial into the disc space. The method further includes inserting a base plate of a second implant trial into the disc space, wherein the second implant trial is coupled to the first implant trial to position the base plate of the first implant trial relative to the base plate of the second implant trial. The method still further includes inserting one or more dilators into the disc space proximate the base plates of the first or second implant trials to distract the first and second vertebrae. The method still further includes removing the base plate of the first implant trial and the dilators from the disc space. The method still further includes inserting the interbody device into the disc space in substantially the same position as the base plate of the first implant trial.

In some embodiments, provided is a method of implanting interbody devices into a disc space located between a first and second vertebra including inserting a base plate of a first implant trial to a selected location at least partially within the disc space, the first implant trial including an elongated body and a base plate coupled to the elongated body. The selected location includes a selected angle with respect to the sagittal plane of the vertebra. The method further includes inserting a first dilator between the base plate of the first implant trial and the first or second vertebra to distract the vertebrae. The method still further includes coupling a first guide member of a guide frame to the elongated body of the first implant trial, the guide frame further including a second guide member. The first and second guide members of the guide frame are rigidly coupled and positioned at a selected convergent angle relative to one another. The method still further includes coupling an elongated body of a second implant trial to the second guide member such that a base plate of the second implant trial is inserted at least partially within the disc space, and such that at least a portion of the base plate of the second implant trial abuts a portion of the base plate of the first implant trial. The method still further includes inserting a second dilator between the base plate of the second implant trial and the first or second vertebra to distract the vertebrae. The method still further includes removing the base plate of the first implant trial and the first dilator from the disc space and uncoupling the elongated body of the first implant trial from the first guide member. The method still further includes, coupling an elongated body of a first insertion instrument to the first guide member such that a first interbody device is inserted at least partially within the disc space in substantially the same position as the base plate of the first implant trial, the first insertion instrument including the elongated body and an insertion member coupled to the elongated body, wherein the insertion member is releasably coupled to the first interbody device. The first interbody device is positioned within the disc space at a selected angle with respect to the sagittal plane of the vertebra. The method still further includes, removing the base plate of the second implant trial and the second dilator from the disc space and uncoupling the elongated body of the second implant trial from the second guide member. The method still further includes, coupling an elongated body of a second insertion instrument to the second guide member such that a second interbody device is inserted at least partially within the disc space in substantially the same position as the base plate of the second implant trial, the second insertion instrument including an elongated body and an insertion member coupled to the elongated body, wherein the insertion member is releasably coupled to the second interbody device. At least a portion of the second interbody device is located at or near the first interbody device. The method still further includes, uncoupling the first interbody device from the insertion member of the first insertion instrument. The method still further includes, uncoupling the second interbody device from the insertion member of the second insertion instrument.

In some embodiments, provided is a system for implanting an interbody device into a disc space located between a first and second vertebra including a guide frame, the guide frame including a guide member having an opening. The system further includes an implant trial including an elongated body and a base plate coupled to the elongated body. The elongated body of the implant trial is releasably coupled to the guide member of the guide frame during use such that the opening guides longitudinal movement of the implant trial relative to the guide frame. The system still further includes a dilator operatively coupled to the elongated body during use for distracting the disc space. The system still further includes an insertion instrument including an elongated body and an insertion member coupled to the elongated body. The elongated body of the insertion instrument is releasably coupled to the guide member of the guide frame during use such that the opening guides longitudinal movement of the insertion instrument relative to the guide frame. The insertion member is releasably coupled to at least a portion of the interbody device during use.

In some embodiments, provided is a system for implanting interbody devices into a disc space located between a first and second vertebra including a guide frame, the guide frame including a first guide member having a first opening and a second guide member have a second opening. The system further includes first and second implant trials each including an elongated body and a base plate coupled to the elongated body. The elongated bodies of the first and second implant trials are releasably coupled to the first and second guide members of the guide frame respectively during use such that the openings of the first and second guide members of the guide frame guide longitudinal movement of the first and second implant trials respectively relative to the guide frame. The system still further includes a dilator operatively coupled to the elongated body of the first or second implant trial during use for distracting the disc space. The system still further includes, first and second insertion instruments each including an elongated body and an insertion member coupled to the elongated body. The elongated bodies of the first and second insertion instruments are releasably coupled to the first and second guide members of the guide frame respectively during use such that the openings of the first and second guide members of the guide frame guide longitudinal movement of the first and second insertion instruments respectively relative to the guide frame. The insertion members of the first and second insertion instruments are each releasably coupled to complementary interbody devices during use.

In some embodiments, provided is a system for implanting an interbody device into a disc space located between a first and second vertebra, including a guide frame, the guide frame including an insertion bridge and first and second guide members. The first and second guide members of the guide frame are rigidly coupled to the insertion bridge and positioned at a convergent angle relative to one another during use. The first and second guide members of the guide frame each include an opening, the openings including a channel with a lateral opening. The first and second guide members of the guide frame each include at least a first portion of a locking mechanism. The system further includes first and second implant trials each including an elongated body and a base plate coupled to the elongated body. The elongated bodies of the first and second implant trials are releasably coupled to the first and second guide members of the guide frame respectively during use such that the respective openings of the first and second guide members of the guide frame guide longitudinal movement of the implant trials relative to the guide frame. The system still further includes, a dilator operatively coupled to the elongated body of the first or second implant trial during use for distracting the disc space. The system still further includes, first and second insertion instruments each including an elongated body and an insertion member coupled to the elongated body. The elongated bodies of the first and second insertion instruments are releasably coupled to the first and second guide members of the guide frame respectively during use. The insertion members of the first and second insertion instruments are releasably coupled to complementary interbody devices during use.

In some embodiments, provided is a system for implanting interbody devices into a disc space located between a first and second vertebra including a guide frame, the guide frame including first and second guide members. The first and second guide members of the guide frame are rigidly coupled to one another and positioned at a selected convergent angle relative to one another during use. The first and second guide members of the guide frame each include openings receiving an elongated body during use. The first and second guide members of the guide frame each include at least a first portion of a locking mechanism fixedly coupling the guide frame to an elongated body during use. The system further includes first and second implant trials each including an elongated body and a base plate coupled to the elongated body. The elongated bodies of the first and second implant trials are releasably coupled to the first and second guide members of the guide frame respectively during use such that the respective openings guide longitudinal movement of the implant trials relative to the guide frame. The elongated bodies are configured to advance laterally into engagement with the openings of the first and second guide members of the guide frame. The system further includes first and second insertion instruments each including an elongated body and an insertion member coupled to the elongated body. The elongated bodies of the first and second insertion instruments are releasably coupled to the first and second guide members of the guide frame respectively during use. The insertion members of the first and second insertion instruments are releasably coupled to complementary interbody devices during use.

In some embodiments, provided is a system for implanting interbody devices into a disc space located between a first and second vertebra including a guide frame, the guide frame including first and second guide members. The system further includes first and second implant trials, the first and second implant trials each including an elongated body. The elongated bodies of the first and second implant trials are releasably coupled to the first and second guide members of the guide frame respectively during use. The first and second implant trials each further include a base plate coupled to the elongated body. The base plate includes an inferior and/or superior surface having a shape that is substantially the same as the shape of an inferior and/or superior surface of an interbody device. The system still further includes a dilator releasably coupled to the elongated body of the first or second implant trial during use such that, the dilator can be uncoupled from the elongated body and replaced with another dilator. The system still further includes first and second insertion instruments each including an elongated body and an insertion member coupled to the elongated body. The elongated bodies of the first and second insertion instruments are releasably coupled to the first and second guide members of the guide frame respectively during use. The insertion members of the first and second insertion instruments are releasably coupled to complementary interbody devices during use.

In some embodiments, provided is a system for implanting interbody devices into a disc space located between a first and second vertebra including a guide frame including first and second guide members. The first and second guide members of the guide frame are rigidly coupled to one another and positioned at a selected convergent angle relative to one another during use. The system further includes first and second implant trials each including an elongated body and a base plate coupled to the elongated body. The elongated bodies of the first and second implant trials are releasably coupled to the first and second guide members of the guide frame respectively during use. The system still further includes first and second dilators releasably coupled to the respective elongated bodies of the first and second implant trials during use such that the first and second dilators can be uncoupled from the elongated bodies of the first and second implant trials and replaced with another dilator. The base plates of the first and second implant trials are coupled to the respective elongated bodies of the first and second implant trials such that, during use, when the elongated bodies of the first and second implant trials are coupled to the respective first and second guide members of the guide frame, and when the base plates of the first and second implant trials are at least partially inserted into the disc space, the base plates of the first and second implant trials are positioned at a substantially equal anterior-posterior depth within the disc space. The system still further includes first and second insertion instruments each including an elongated body and an insertion member coupled to the elongated body. The elongated bodies of the first and second insertion instruments are releasably coupled to the first and second guide members of the guide frame respectively during use. The insertion members of the first and second insertion instruments are releasably coupled to complementary interbody devices during use.

In some embodiments, provided is a system for implanting interbody devices into a disc space located between a first and second vertebra including a guide frame, the guide frame including an insertion bridge and first and second guide members. The first and second guide members of the guide frame are rigidly coupled to the insertion bridge and positioned at a selected convergent angle relative to one another during use. The first and second guide members of the guide frame each include an opening, the openings including a channel with a lateral opening. The first and second guide members of the guide frame each include a first portion of a locking mechanism. The system further includes first and second implant trials including an elongated body and a base plate coupled to the elongated body. The elongated body of the first implant trial is slidable through the opening of the first guide member and the elongated body of the second implant trial is slidable through the opening of the second guide member. The elongated bodies of the first and second implant trials each include a second portion of the locking mechanism, such that, during use, when the first and second portions of the locking mechanism are engaged, the first and second guide members of the guide frame are fixedly coupled to the respective elongated bodies of the first and second implant trials at a selected location on the elongated bodies of the first and second implant trials. The first and second implant trials each include a longitudinal slot. The system still further includes a dilator operatively coupled to the elongated body of the first or second implant trial during use for distracting the disc space. The dilator is located in the longitudinal slot of the first or second implant trial. The system still further includes first and second insertion instruments including an elongated body and an insertion member coupled to the elongated body. The elongated body of the first insertion instrument is slidable through the opening of the first guide member and the elongated body of the second insertion instrument is slidable through the opening of the second guide member. The elongated bodies of the first and second insertion instruments each include the second portion of the locking mechanism, such that, during use, when the first and second portions of the locking mechanism are engaged, the first and second guide members of the guide frame are fixedly coupled to the respective elongated bodies of the first and second insertion instruments at a selected location on the elongated bodies of the first and second insertion instruments. The insertion members of the first and second insertion instruments are releasably coupled to respective complementary interbody devices during use.

In some embodiments, provided is an apparatus for implanting an interbody device into a disc space located between a first and second vertebra including a guide frame, the guide frame including an insertion bridge and first and second guide members. The first and second guide members of the guide frame are rigidly coupled to the insertion bridge and positioned at a convergent angle between about 20° to 30° relative to one another during use. The first and second guide members of the guide frame each include openings receiving an elongated body during use, the openings including a channel with a lateral opening. The first and second guide members of the guide frame each include at least a first portion of a locking mechanism fixedly coupling the guide frame to an elongated body during use.

In some embodiments, provided is an apparatus for implanting an interbody device into a disc space located between a first and second vertebra including an implant trial, the implant trial including an elongated body. The implant trial further including a base plate coupled to the elongated body during use. The base plate includes an inferior and/or superior surface having a shape that is substantially the same as the shape of an inferior and/or superior surface of an interbody device. The implant trial still further including a dilator releasably coupled to the elongated body during use such that the dilator can be uncoupled from the elongated body and replaced with another dilator. The implant trial still further includes a nerve root shield coupled to the elongated body during use. The nerve root shield includes a surface that is shaped complementary to a surface of the first or second vertebra.

BRIEF DESCRIPTION OF THE DRAWINGS

Advantages of the present invention will become apparent to those skilled in the art with the benefit of the following detailed description and upon reference to the accompanying drawings in which:

FIG. 14 is a front perspective view of an implant trial in accordance with one or more embodiments of the present technique;

FIG. 15 is a rear perspective view of the implant trial in accordance with one or more embodiments of the present technique;

FIG. 16 is a side view of a lower portion of the implant trial in accordance with one or more embodiments of the present technique;

FIG. 19 is a perspective view of a guide frame in accordance with one or more embodiments of the present technique;

FIG. 20 is a top view of a guide member of the guide frame with a guide release in a first position in accordance with one or more embodiments of the present technique;

FIG. 21 is a top view of the guide member of the guide frame with a guide release in a second position in accordance with one or more embodiments of the present technique;

Figure 1:
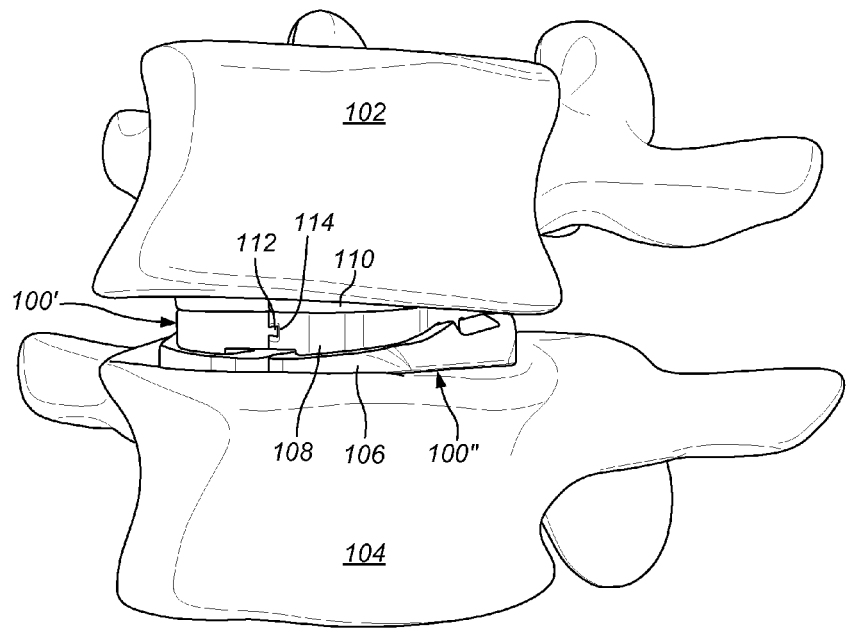
FIG. 1 is a perspective view of two dynamic interbody devices positioned between vertebrae in accordance with one or more embodiments of the present technique.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION

A "functional spinal unit" generally refers to a motion segment of a spine. The functional spinal unit may include two vertebrae, an intervertebral disc between the vertebrae, and the two facet joints between the vertebrae. An "artificial functional spinal unit" refers to a functional spinal unit where one or more of the components of the functional spinal unit are replaced by implants or devices that permit at least some motion of the spine. At least a portion of the intervertebral disc and/or one or both of the facet joints may be replaced by implants or devices during a spinal stabilization procedure.

As used herein, "coupled" includes a direct or indirect joining or touching unless expressly stated otherwise. For example, a first member is coupled to a second member if the first member contacts the second member, or if a third member is positioned between the first member and the second member.

An "interbody device" generally refers to an artificial intervertebral implant. The interbody device may replace a portion or all of an intervertebral disc. In some embodiments, a pair of interbody devices is installed during a spinal stabilization procedure. In some embodiments, one or more interbody devices are installed using a posterior approach. In other embodiments, one or more interbody devices may be installed using an anterior approach or other type of approach. In some embodiments, one or more interbody devices are placed in a disc space between vertebrae, and at least one posterior stabilization system is coupled to the vertebrae. In some embodiments, one or more interbody devices are placed in the disc space without coupling a posterior stabilization system to the vertebrae.

A "fusion interbody device" generally refers to an interbody device that facilitates fusion of adjacent vertebrae coupled to the device. A fusion device may provide stabilization of adjacent vertebra to at least partially inhibit movement of the vertebra to facilitate bone growth to fuse the adjacent vertebra.

A "dynamic interbody device" generally refers to an interbody device that allows for flexion/extension, lateral bending and/or axial rotation of vertebrae coupled to the device.

In some embodiments, the dynamic interbody device is a bimodal device. Bimodal refers to a device that has at least two separate curved surfaces to accommodate flexion/extension with lateral bending and/or axial rotation.

Dynamic interbody devices may have surfaces that contact vertebrae. In some embodiments, a surface of the dynamic interbody device that contacts a vertebra may include one or more anchors, protrusions, and/or osteoconductive/osteoinductive layers or coatings. A anchor of the dynamic interbody device may be positioned in an aperture formed in a vertebra. The aperture may be formed in the vertebra so that the dynamic interbody device will be positioned at a desired location when inserted into the patient.

In some embodiments, one or more dynamic interbody devices are installed in a disc space formed between vertebrae during a spinal stabilization procedure. The shape and/or size of a dynamic interbody device may depend on a number of factors including surgical approach employed for insertion, intended position in the spine (e.g., cervical or lumbar), and patient anatomy. As described in U.S. Patent Publication No. 2009/0105829 to Gimbel et al., several sizes of interbody devices may be provided in the instrument kit for the spinal stabilization procedure. The dynamic interbody devices may include indicia indicating the height of the spinal stabilization devices.

The dynamic interbody devices may allow for flexion/extension, axial rotation, and/or lateral bending of vertebrae coupled to the dynamic interbody device.

The dynamic interbody device may allow for coupled lateral bending and axial rotation so that axial rotation causes some lateral bending and lateral bending causes some axial rotation. The dynamic interbody device may be formed so that a set amount of lateral bending results in a set amount of axial rotation.

In some embodiments, a pair of dynamic interbody devices may be installed between two vertebrae to establish all or a portion of a spinal stabilization system. Each dynamic interbody device of the pair of dynamic interbody devices may be installed using a posterior approach.

As used herein a "dynamic posterior stabilization system" generally refers to an apparatus that may be used to at least partially replace or supplement a facet joint while allowing for both dynamic resistance and at least some motion of the first vertebra to be stabilized relative to the second vertebra to be stabilized. The first vertebra and the second vertebra may be vertebrae of a functional spinal unit. In some embodiments, bone fasteners of the dynamic posterior stabilization system are secured to the first vertebra and the second vertebra. In some embodiments, a bone fastener of the dynamic posterior stabilization system may be coupled to a vertebra adjacent to the vertebrae of the functional spinal unit being stabilized. The bone fasteners may be coupled to lamina, pedicles, and/or vertebral bodies of the vertebrae. In some embodiments, dynamic posterior stabilization systems may be positioned in three or more vertebrae to form a multi-level stabilization system.

The dynamic posterior stabilization system may replace or supplement a normal, damaged, deteriorated, defective or removed facet joint. The dynamic posterior stabilization system may include bone fasteners, an elongated member, and at least one bias member. The bias member may provide little or no initial resistance to movement of a first vertebra coupled to the system relative to a second vertebra coupled to the system. Resistance to additional movement of the first vertebra relative to the second vertebra may increase. The increasing resistance provided by the bias member may mimic the behavior of a normal functional spinal unit. The dynamic posterior stabilization system may stabilize the vertebrae, limit the range of motion of the first vertebra relative to the second vertebra, and/or share a portion of the load applied to the vertebrae. The dynamic posterior stabilization system may work in conjunction with one or more interbody devices to provide support provided by a natural facet. For example, a dynamic interbody device may provide for coupled lateral bending and axial rotation of the adjacent vertebra as well as enable flexion and extension, while the posterior stabilization system provides for controlled/dampened lateral bending, axial rotation, flexion and extension of the adjacent vertebra.

In some embodiments, dynamic interbody devices and dynamic posterior stabilization systems may be made of non-magnetic, radiolucent materials to allow unrestricted intra-operative and post-operative imaging. Certain material may interfere with x-ray and/or magnetic imaging. Magnetic materials may interfere with magnetic imaging techniques. Most non-magnetic stainless steels and cobalt chrome contain enough iron and/or nickel so that both magnetic imaging and x-ray imaging techniques are adversely affected. Other materials, such as titanium and some titanium alloys, are substantially iron free. Such materials may be used when magnetic imaging techniques are to be used, but such materials are often radio-opaque and sub-optimal for x-ray imagining techniques. Many ceramics and polymers are radiolucent and may be used with both magnetic imaging techniques and x-ray imaging techniques. The dynamic interbody devices and/or the dynamic posterior stabilization systems may include coatings and/or markers that indicate the positions of the devices and/or systems during operative and/or post-operative imaging.

In some embodiments, two cooperative interbody devices (e.g., fusion or dynamic interbody devices) may be positioned in a disc space between two vertebrae during a spinal stabilization procedure. FIG. 1 is a perspective view of two interbody devices 100', 100" positioned between vertebrae 102, 104 in accordance with one or more embodiments of the present technique. In the illustrated embodiment, interbody devices 100', 100" includes dynamic interboyde devices. Dynamic interbody devices 100', 100" may be implanted using a posterior approach. Anterior ends and/or posterior ends of dynamic interbody devices 100', 100" may be positioned near the edge of the endplates of vertebrae 102, 104 so that the dynamic interbody devices abut strong, supportive bone of the vertebrae to be stabilized. Dynamic interbody devices 100', 100" may be bilateral devices with coupled axial rotation and lateral bending. Although several embodiments are discussed with regard to dynamic interbody devices, the same or similar techniques may be employed for inserting other types of implants, such as fusion interbody devices (e.g., spinal fusion implants). For example, interbody devices 100' and 100" may include fusion interbody devices in place of dynamic interbody devices described herein.

Figure 2:
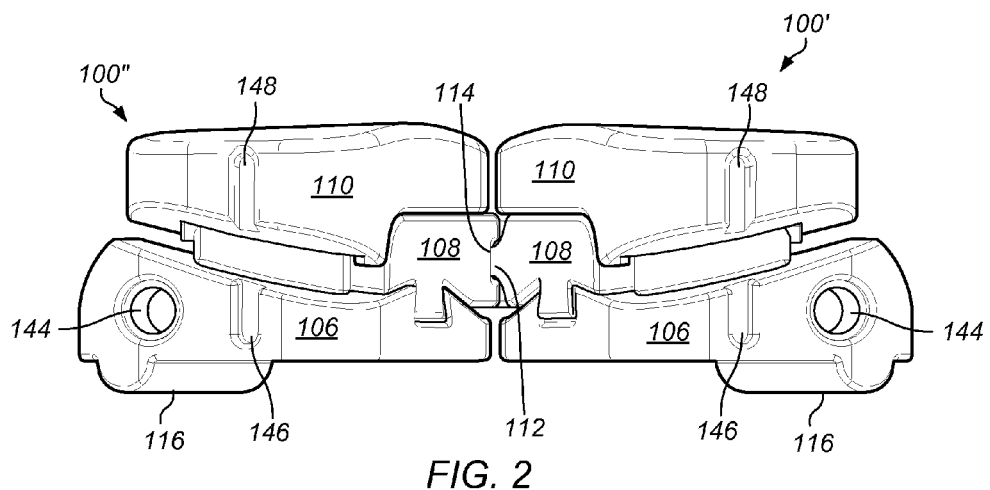
FIG. 2 is a rear view of the two dynamic interbody devices in accordance with one or more embodiments of the present technique.

FIG. 2 is a rear view of dynamic interbody devices 100', 100" in accordance with one or more embodiments of the present technique. Each dynamic interbody device 100' or 100" may include first member 106, second member 108 and third member 110. First members 106 may be coupled to second members 108 so that dynamic interbody devices 100', 100" accommodate lateral bending and axial rotation of vertebrae coupled to the dynamic interbody devices. In some embodiments, dynamic interbody devices 100', 100" couple lateral bending and axial motion together so that lateral bending motion causes axial rotation, and axial rotation causes lateral bending. Third members 110 may be coupled to second members 108 so that dynamic interbody device 100', 100" accommodate flexion and extension of vertebrae coupled to the dynamic interbody device. Dynamic interbody devices 100', 100" are shown in positions of neutral lateral bending, neutral axial rotation and maximum flexion in FIG. 2. In some embodiments, the first members are coupled to the second members to allow for lateral bending without coupled axial rotation and/or axial rotation without coupled lateral bending.

In some embodiments, first member 106 of dynamic interbody device 100' may be substantially a mirror image first member 106 of dynamic interbody device 100", and third member 110 of dynamic interbody device 100' may be substantially a mirror image of third member 110 of dynamic interbody device 100". In other embodiments, the first member of dynamic interbody device 100' may have a shape that is different than the mirror image of the first member of dynamic interbody device 100" and/or the third member of dynamic interbody device 100' may have a shape that is different than the mirror image of the third member of dynamic interbody device 100".

Second member 108 of dynamic interbody device 100' may be substantially the mirror image of second member 108 of dynamic interbody device 100" with the exception of second member 108 of dynamic interbody device 100' having portion 112 (e.g., a protrusion) that engages a complementary portion 114 (e.g., a recess) of second member 108 of dynamic interbody device 100" to join dynamic interbody device 100' to dynamic interbody device 100" when the dynamic interbody devices are positioned between vertebrae. In other embodiments, first member 106 of dynamic interbody device 100' has a portion (e.g., a protrusion) that engages a portion (e.g., a recess) of first member 106 of dynamic interbody device 100" when the dynamic interbody devices are positioned between vertebrae. In other embodiments, third member 110 of dynamic interbody device 100' has a portion (e.g., a protrusion) that engages a portion (e.g., a recess) of first member 110 of dynamic interbody device 100" when the dynamic interbody devices are positioned between vertebrae.

Figure 3:
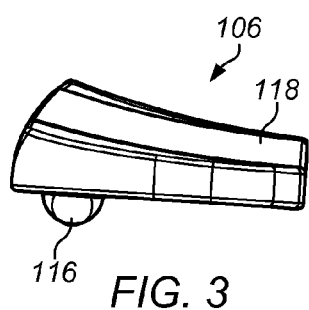
FIG. 3 is a front view of a first member of a dynamic interbody device in accordance with one or more embodiments of the present technique.
Figure 4:
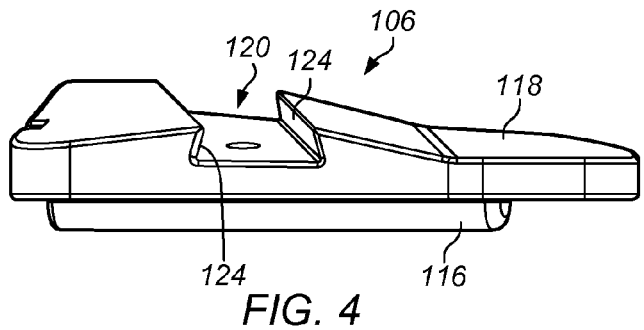
FIG. 4 is a side view of the first member of the dynamic interbody device in accordance with one or more embodiments of the present technique.
Figure 5:
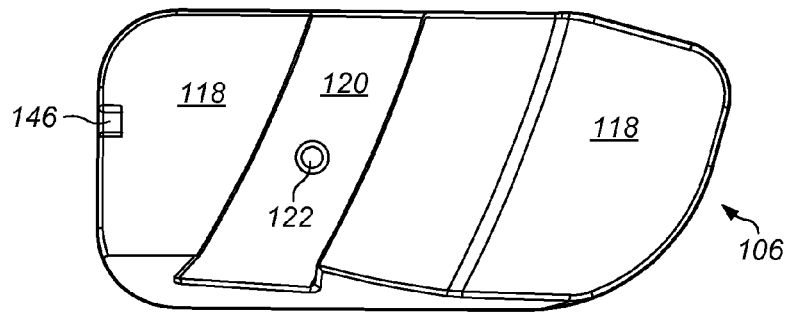
FIG. 5 is a top view of the first member of the dynamic interbody device in accordance with one or more embodiments of the present technique.
Figure 6:
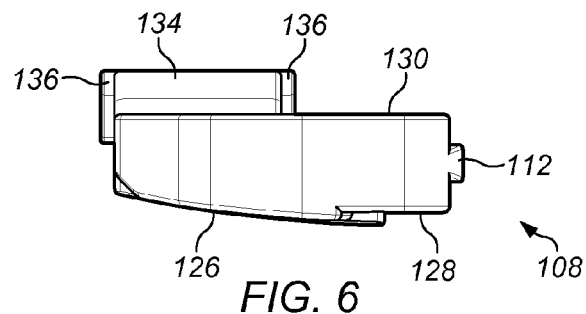
FIG. 6 is a front view of a second member of the dynamic interbody device in accordance with one or more embodiments of the present technique.

FIGS. 3-5 are front, side and top views, respectively, of first member 106 of dynamic interbody device 100' in accordance with one or more embodiments of the present technique. First member 106 may include anchor 116 (e.g., a keel or the like), superior surface 118, slot 120, and opening 122. Anchor 116 may reside in an aperture or recess formed in a vertebra when dynamic interbody device 100' is positioned in a disc space between vertebrae. Anchor 116 may inhibit undesired movement of dynamic interbody device 100' relative to the vertebrae. Superior surface 118 of first member 106 may be curved. The curvature of superior surface 118 may complement a curvature of an inferior surface of the second member of the dynamic interbody device to allow the dynamic interbody device to accommodate lateral bending.

First member 106 may include arcuate slot 120. Arcuate slot 120 may interact with a complementary protrusion of second member 108 to allow the dynamic interbody device to accommodate axial rotation. The curvature of superior surface 118 and arcuate slot 120 allows dynamic interbody device 100' to provide coupled lateral bending and axial rotation to the vertebrae adjacent to the dynamic interbody device. In some embodiments, second member 108 may have an arcuate slot and first member 106 may have a complementary protrusion.

Arcuate slot 120 and the protrusion of second member 108 may be dovetailed or include another type of interconnection system that inhibits non-rotational separation of first member 106 from second member 108 when the protrusion of the second member is engaged in slot 120 of the first member. End surfaces 124 of arcuate slot 120 may interact with the end surfaces of the protrusion of second member 108 to resist shear load applied to dynamic interbody device 100' when the dynamic interbody device is positioned between vertebrae. End surfaces 124 and the end surfaces of the protrusion of second member 108 may be guides for lateral bending and axial rotation of the vertebrae coupled to dynamic interbody device 100'.

First member 106 may include opening 122 in slot 120. A pin may be positioned in opening 122. The pin may reside in a groove in second member 108 to define the maximum amount of lateral bending/axial rotation allowed by dynamic interbody device 100'. In other embodiments, a pin positioned in an opening in second member 108 may reside in a groove in first member 106 to define the maximum amount of lateral bending/axial rotation allowed by dynamic interbody device 100'.

FIGS. 6-10 are front, side, top, bottom and perspective views, respectively of second member 108 of dynamic interbody device 100' in accordance with one or more embodiments of the present technique. Second member 108 may include inferior surface 126, recessed surface 128, superior surface 130, protrusion 132, bearing 134, tabs 136, groove 138, and portion 112. Some of inferior surface 126 may rest on superior surface 118 of first member 106 when protrusion 132 is placed in the arcuate slot 120 of the first member. Inferior surface 126 may include a curvature that complements the curvature of superior surface 118 of first member 106 and protrusion 132 may complement the arcuate slot in the first member so that dynamic interbody device 100' is able to accommodate coupled lateral bending and axial rotation of the vertebra joined to the dynamic interbody device.

Figure 10:
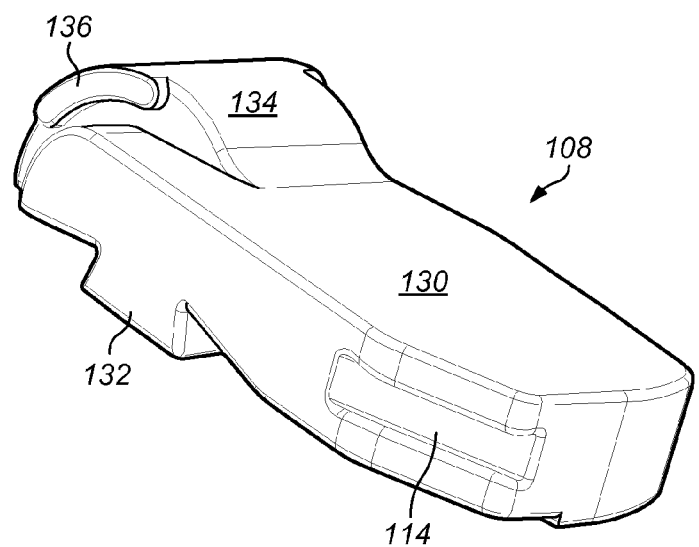
FIG. 10 is a perspective view of the second member of the dynamic interbody device in accordance with one or more embodiments of the present technique.

Portion 112 of second member 108 of dynamic interbody device 100' (shown in FIGS. 1 and 6) may engage a complementary portion of second member 108 of second dynamic interbody device 100" positioned adjacent to dynamic interbody device 100' when dynamic interbody devices 100', 100" are positioned in a disc space between vertebrae. FIG. 10 depicts second member 108 with portion 114 that complements portion 112 of second member shown in FIG. 6. Engaging portion 112 of dynamic interbody device 100' with complementary portion 114 of dynamic interbody device 100" may stabilize and align the dynamic interbody devices when the dynamic interbody devices are positioned between vertebrae. Coupling and aligning dynamic interbody devices 100', 100" together with portions 112, 114 may assure that the second members of the dynamic interbody devices move in tandem relative to the first members of the dynamic interbody devices.

Coupling dynamic interbody devices 100', 100" together with portions 112, 114 may inhibit migration of the dynamic interbody devices and/or subsidence of the vertebrae coupled to the dynamic interbody devices. Having complementary portions may require that a specific dynamic interbody device be installed prior to the other dynamic interbody device during an insertion procedure. For example, the dynamic interbody device with a female connection portion (i.e., portion 114 in FIG. 10) may need to be installed first. After insertion, migration and/or removal of the dynamic interbody devices is only possible by reversing the insertion order with the two dynamic interbody devices held in the same position as during insertion (i.e., neutral in axial rotation and lateral bending while in full flexion). Proper positioning of the two dynamic interbody devices may be determined by examining the position of the connected portions using imaging techniques before removal of the insertion instruments.

Figure 7:
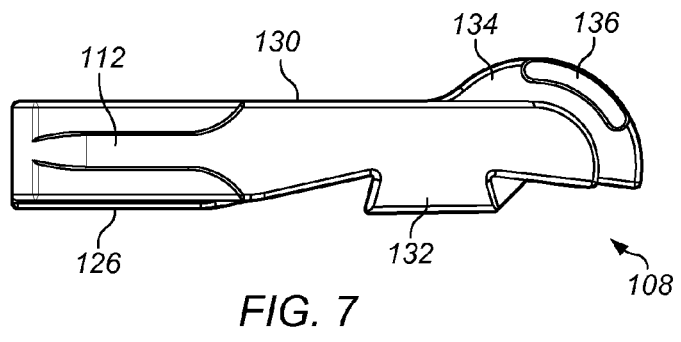
FIG. 7 is a side view of the second member of the dynamic interbody device in accordance with one or more embodiments of the present technique.
Figure 8:
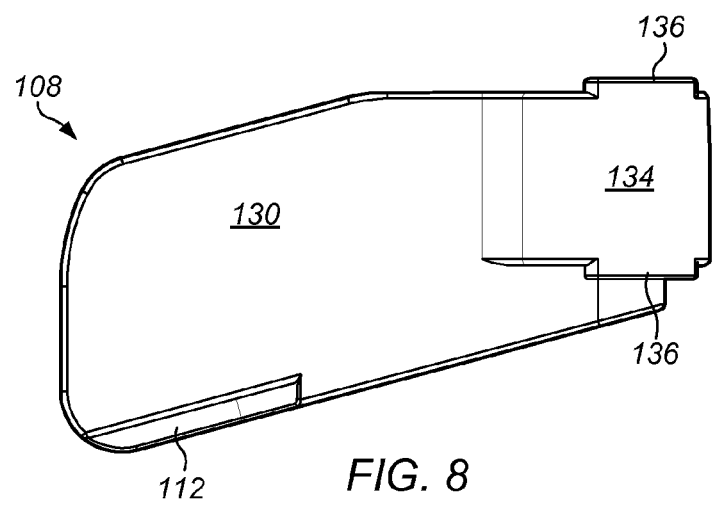
FIG. 8 is a top view of the second member of the dynamic interbody device in accordance with one or more embodiments of the present technique.

As shown in FIG. 7, second member 108 may include bearing 134. Bearing 134 may fit in a recess of third member 110 to allow the dynamic interbody device to accommodate flexion and extension of the vertebra coupled to the dynamic interbody device. Bearing 134 may include tabs 136. Tabs 136 may fit in tracks in third member 110 to inhibit separation of second member 108 from the third member. To assemble the dynamic interbody device, third member 110 may be coupled to second member 108, and/or second member 108 may be coupled to first member 106. The first member will inhibit separation of the third member from the second member even when the dynamic interbody device is subjected to the maximum amount of extension.

Figure 9:
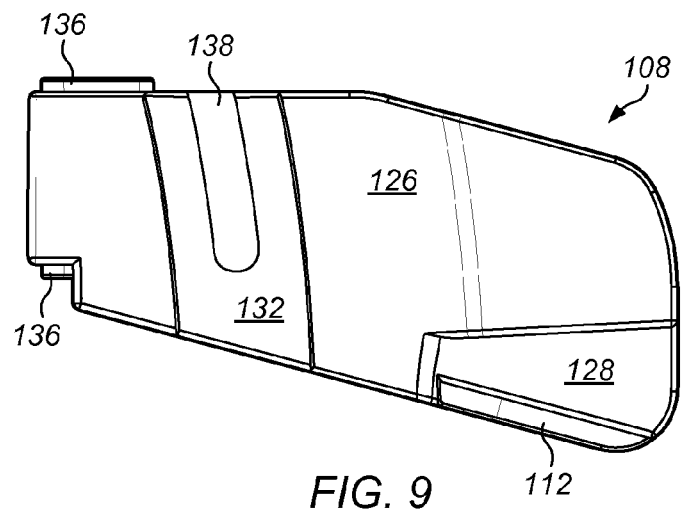
FIG. 9 is a bottom view of the second member of the dynamic interbody device in accordance with one or more embodiments of the present technique.

As shown in FIG. 9, groove 138 may be formed in protrusion 132 of second member 108. In some embodiments, groove 138 may be open at one side of second member 108. A pin in opening 112 of first member 106 may reside in groove 138 of the assembled dynamic interbody device.

Second member 108 may include recessed surface 128 in inferior surface 126. Recessed surface 128 may allow a portion of second member 108 to extend over a portion of first member 106 of second dynamic interbody device 100" without interference during lateral bending.

Figure 11:
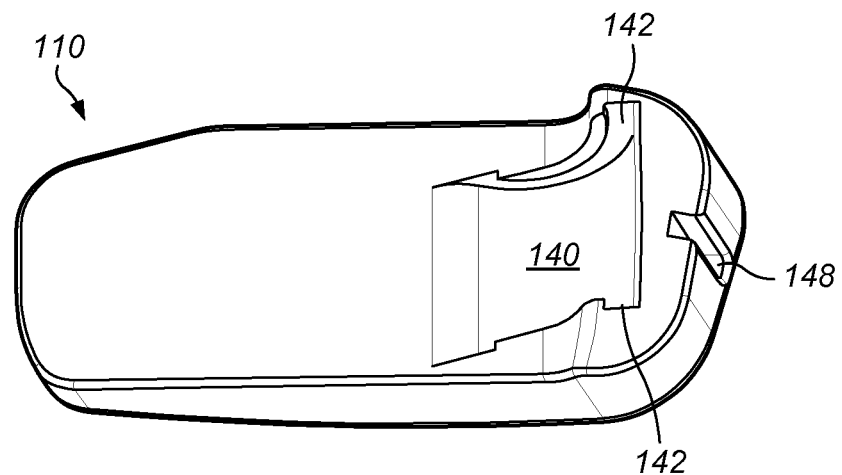
FIG. 11 is a perspective view of the third member of the dynamic interbody device in accordance with one or more embodiments of the present technique.

FIG. 11 is a perspective view of third member 110 of dynamic interbody device 100' in accordance with one or more embodiments of the present technique. Third member 110 may include recess 140 with tracks 142. Recess 140 and tracks 142 may complement the bearing and tabs of the second member.

As shown in FIG. 2, first member 106 of each dynamic interbody device 100', 100" may include opening 144. Opening 144 may accept a complementary portion of another device. Opening 144 may be a threaded opening or have another type of releasable coupling mechanism. Opening 144 may be used to releasably couple dynamic interbody device 100' or 100" to an insertion instrument used for placing dynamic interbody device within an intervertebral disc space. In other embodiments, openings for the insertion instrument may be located in second member 108 and/or the third member 110.

The dynamic interbody device may include one or more features that allow the insertion instrument to hold the dynamic interbody device in a desired position. For example, first member 106 may include slot 146 and third member 110 may include slot 148. In some embodiments, slots 146, 148 may include other types of depressions such as a round hole or elongated slot for accepting a complementary portion of insertion instrumentation. A portion of the insertion instrument may be placed in slots 146, 148. The portion of the insertion instrument that fits in slots 146, 148 may place the dynamic interbody device in a desired position for insertion between vertebrae (i.e., neutral axial rotation, neutral lateral bending, and full flexion). For example, a pin of an insertion instrumentation placed in both of slots 148 and 146 may fix relative rotational/bending/flexion positions of first member 106, second member 108 and/or third member 110 such that they may be held in a relatively fixed position during insertion into the intervertebral disc space.

Figure 24:
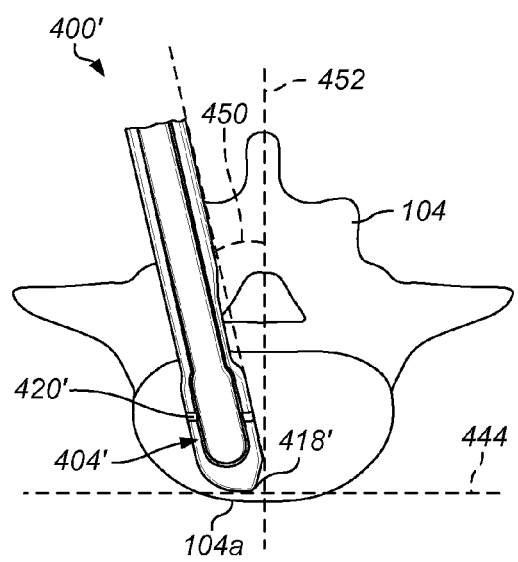
FIG. 24 is a front view of a lower portion of the implant trial of FIG. 23 with the base plate inserted into a disc space between vertebrae in accordance with one or more embodiments of the present technique.
Figure 25:
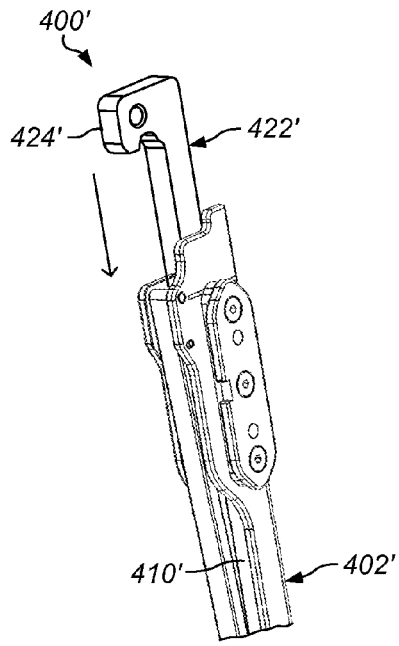
FIG. 25 is a perspective view of an upper portion of the implant trial of FIG. 23 depicting a dilator being coupled to the implant trial in accordance with one or more embodiments of the present technique.
Figure 26:
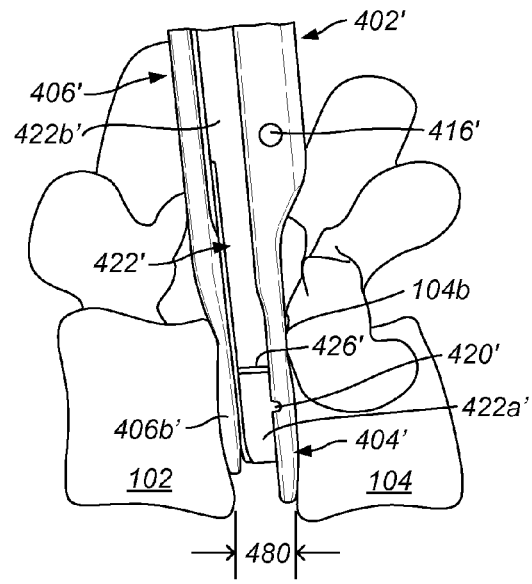
FIG. 26 is a side view of a lower portion of the implant trial of FIG. 23 having a base plate inserted into a disc space between vertebrae and including a dilator in accordance with one or more embodiments of the present technique.
Figure 27:
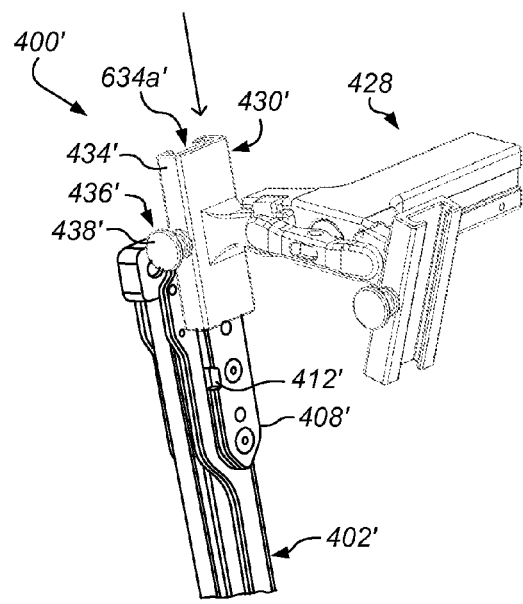
FIG. 27 is a perspective view of an upper portion of the implant trial of FIG. 23 depicting a guide member being coupled to the implant trial in accordance with one or more embodiments of the present technique.

Dynamic interbody devices 100', 100" may work in conjunction to allow for coupled lateral bending and axial rotation and/or flexion/extension of vertebrae 102, 104 the dynamic interbody devices are positioned between. During an insertion procedure, careful positioning of the dynamic interbody devices 100', 100" may be needed to ensure that dynamic interbody device 100' works in conjunction with dynamic interbody device 100". In some dynamic interbody device embodiments, a separation angle of about 30° (i.e., each implant oriented at about 15° from a center line (See angle 450 of FIG. 24) of endplate of the inferior vertebra being stabilized) is desired between dynamic interbody devices 100', 100". In some dynamic interbody device embodiments, a separation angle of about 24° (i.e., each implant oriented at about 12° from a center line (See angle 450 of FIG. 24) of endplate of the inferior vertebra being stabilized) is desired between dynamic interbody devices 100', 100". Other embodiments of dynamic interbody devices may be designed to operate in conjunction with each other at other separation angles.

In some embodiments, insertion instruments may allow insertion of dynamic interbody devices 100', 100" so that ends of the dynamic interbody devices touch. Intra-operative imaging may be used to ensure the proper positioning and alignment of the dynamic interbody devices. In some embodiments, a portion of dynamic interbody device 100' may engage a portion of dynamic interbody device 100" to ensure proper positioning of the dynamic interbody devices 100', 100". For example, a dovetailed portion of dynamic interbody device 100' fits in a complementary groove of dynamic interbody device 100" when the dynamic interbody devices are properly positioned. Engaging dynamic interbody devices may inhibit migration of the dynamic interbody devices after insertion.

The superior surface of the dynamic interbody device may be coupled to an upper vertebra of the vertebrae to be stabilized. An inferior surface of the dynamic interbody device may be coupled to the inferior vertebra of the vertebrae to be stabilized. At least a portion the superior surface may be positioned near the edge of the endplate of the upper vertebra so that the dynamic interbody device abuts strong, supportive bone of the upper vertebra. At least a portion of the inferior surface may be positioned near the edge of the endplate of the inferior vertebra so that the dynamic interbody device abuts strong, supportive bone of the inferior vertebra.

Figure 12:
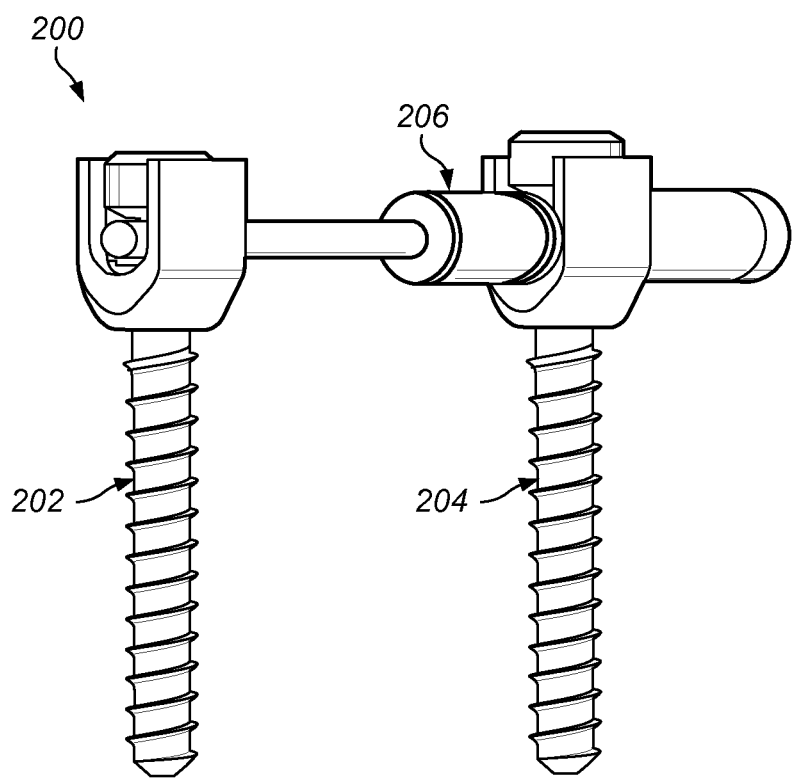
FIG. 12 is a perspective view of a posterior stabilization system in accordance with one or more embodiments of the present technique.

Dynamic posterior stabilization systems may be used to support vertebrae and/or to provide resistance to motion of a first vertebra relative to a second vertebra. FIG. 12 is a perspective view of a posterior stabilization system 200 in accordance with one or more embodiments of the present technique. Posterior stabilization system 200 may be an in-line dynamic posterior stabilization system 200. Dynamic posterior stabilization system 200 may include first bone fastener 202, second bone fastener 204, and dampener system 206. Embodiments of a dynamic posterior stabilization system are further described in U.S. Patent Publication No. 2009/0105829 to Gimbel et al.

Figure 13:
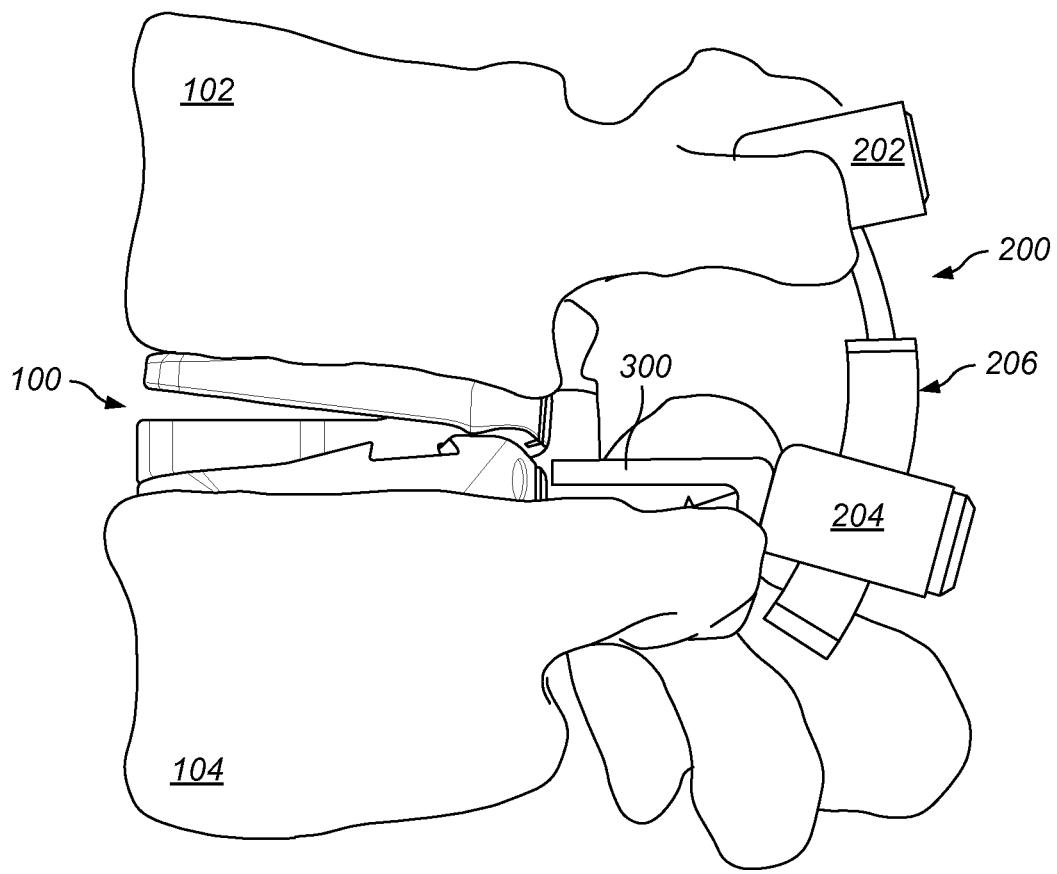
FIG. 13 is a side view of a dynamic interbody device and a posterior stabilization system coupled to vertebrae in accordance with one or more embodiments of the present technique.

FIG. 13 is a side view of dynamic interbody device 100 and posterior stabilization system 200 positioned between vertebrae 102, 104 in accordance with one or more embodiments of the present technique.

Dynamic posterior stabilization system 200 may share a portion of the load applied to vertebrae 102, 104 while providing guidance and resistance to flexion/extension and/or lateral bending that is, or is approximate to, the resistance provided by a normal functional spinal unit. Allowing for movement of the dynamic interbody device and for movement of the dynamic posterior stabilization system may inhibit deterioration of adjacent functional spinal units.

Bridge 300 may be coupled to second bone fastener 204 of dynamic posterior stabilization system 200. Bridge 300 may inhibit undesired migration of dynamic interbody device 100 relative to vertebrae 102, 104 while still allowing for flexion, extension, lateral bending, and/or axial rotation of the vertebrae. Bridge 300 may couple dynamic interbody device 100 to dynamic posterior stabilization system 200. Bridge 300 may be coupled to dynamic posterior stabilization system 200 at or near to second bone fastener 204. Coupling bridge 300 to dynamic posterior stabilization system 200 at or near to second bone fastener 204 may inhibit or eliminate contact of the bridge with neural structure exiting from between the vertebrae. In some embodiments, a bridge may not be provided.

In some embodiments, a posterior approach may be used to install a stabilization system for a patient. The stabilization system may replace one or more parts of a functional spinal unit of the patient. The stabilization system may include one or more dynamic interbody devices, and one or more dynamic posterior stabilization systems.

A discectomy may provide a disc space between two vertebrae in which one or more interbody devices may be implanted. In some embodiments, after a discectomy, two implant trials may be inserted into the disc space between the vertebrae. The implant trials may facilitate proper insertion of one or more dynamic interbody devices into the disc space. For example, the implant trials may be used to properly align and position the dynamic interbody devices within the disc space. Additionally, the implant trials may be used to separate or distract the vertebrae to allow insertion of the dynamic interbody devices into the disc space. The implant trials may be inserted on opposite sides of the sagittal plane of the vertebrae. The implant trial used on one side of the sagittal plane may be a mirror image of the implant trial used on the other side.

FIGS. 14-18 depict various views of an implant trial 400 in accordance with one or more embodiments of the present technique. Implant trial 400 may include elongated body 402, base plate 404, and nerve root shield 406. Nerve root shield 406 may include elongated portion 406a and shielding portion 406b. During use, when the implant trial 400 is inserted into the disc space, shielding portion 406b may be located superiorly to base plate 404. Nerve root shield 406 may abut portions of the vertebra during insertion. For example, shielding portion 406b may about an end plate of the vertebrae and shielding portion 406a may contact a posterior edge portion of the vertebrae proximate the endplate as implant trial 400 is advanced into the intervertebral space adjacent the vertebrae. Nerve root shield 406 may inhibit contact of other portions (e.g., body 402) with the vertebrae.

Elongated body 402 may be any physical structure, having more length than width, capable of at least partially supporting another object. Additionally, elongated body 402 may have any suitable shape. For example, in the illustrated embodiment, elongated body 402 includes a combination of straight and curved surfaces. Elongated body 402 may include key 408, slot 410, pin catch 412, channel/groove 414, and aperture 416. Key 408 may ensure that only a proper guide member can be used in association with the implant trial 400. For example, key 408 may have an external shape that is complementary to an internal shape of the proper (e.g., right or left) guide member. Slot 410 may be located between a portion of elongated body 402 and elongated portion 406a of nerve root shield 406. During use, a dilator may be inserted through slot 410 (thereby coupling the dilator to the implant trial) to distract the disc space. Pin catch 412 may form a portion of a locking mechanism. Pin catch 412 in conjunction with one or more other portions of the locking mechanism may couple implant trial 400 to the guide member and fix the position of the implant trial relative to the guide member (and vice versa). For example, pin catch 412 may receive a complementary biased stop pin of the proper guide member. Channel/groove 414 may extend from the distal end of elongated body 402 to the proximal end of elongated body 402. Channel/groove 414 may be substantially parallel to a longitudinal axis of body 402. A drill bit or other type of cutting tool (e.g., an end mill, countersink, or reamer) may be inserted through channel/groove 414 to form an aperture in the inferior vertebra for accommodating the anchor of a dynamic interbody device. Aperture 416 may extend laterally through elongated body 402 when the implant trial 400 is inserted into the disc space. In some embodiments, aperture 416 may be perpendicular or oblique to a longitudinal axis of body 402. In some embodiments, a true lateral image of the implant trial 400 may be achieved by aligning imaging equipment with aperture 416.

Base plate 404 may be coupled to elongated body 402. Base plate 404 may include inferior surface 404a and superior surface 404b. Inferior surface 404a may have a shape that is substantially the same as the shape of an inferior surface of a dynamic interbody device (e.g., inferior surface of first member 106 of dynamic interbody device 100'). Base plate 404 may further include x-ray visible features 418 and 420. The location of x-ray visible feature 418 within the disc space may correspond to the approximate location of the anterior edge of a dynamic interbody device when the device is inserted into the disc space in place of base plate 404. That is, x-ray visible feature 418 may indicate the approximate expected location of the anterior edge of the dynamic interbody device being inserted subsequent to positioning of implant trial. For example, if base plate 404, coupled to elongated body 402, is removed from the disc space and the dynamic interbody device, coupled to the insertion member of an insertion instrument, is inserted into the disc space via the same guide member as base plate 404, then the anterior edge of the dynamic interbody device may be located at approximately the same anterior-posterior depth within the disc space as was x-ray visible feature 418. Similarly, x-ray visible feature 420 may indicate the approximate expected location of the center of rotation of the dynamic interbody device. Thus, advantageously, the dynamic interbody device may be inserted between the vertebrae in proper alignment by correctly positioning the x-ray visible features of base plate 404 within the disc space. In some embodiments, implant trial 400 may include one or more additional features that are visible via intra-operative techniques (e.g., x-ray, computed tomography, ultrasound, and magnetic resonance imaging).

Figure 17:
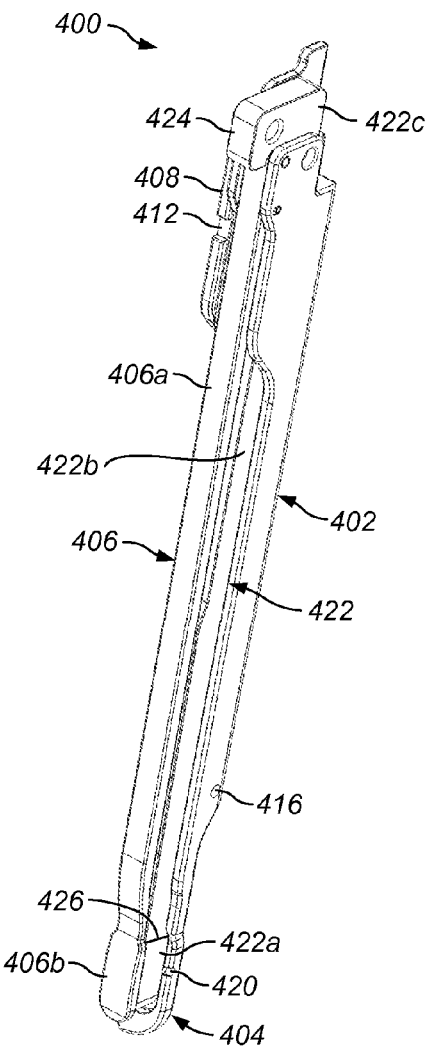
FIG. 17 is a perspective view of the implant trial including a dilator in accordance with one or more embodiments of the present technique.
Figure 18:
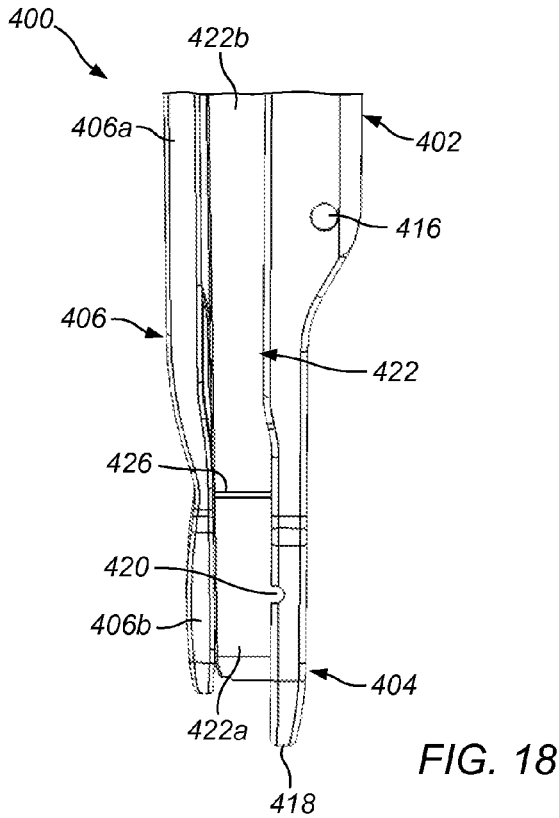
FIG. 18 is a side view of a lower portion of the implant trial including a dilator in accordance with one or more embodiments of the present technique.

In some embodiments, one or more dilators 422 may be used to distract the disc space. FIGS. 17 and 18 are perspective and side views, respectively, of implant trial 400 including dilator 422 in accordance with one or more embodiments of the present technique. As depicted in FIGS. 17 and 18, one or more dilators 422 may be positioned between base plate 404 and nerve root shield 406 to facilitate separation of the vertebrae. In some embodiments, with a leading end of insertion instrument 400 disposed in a vertebral space between adjacent vertebra, insertion of dilator 422 may spread inferior and superior surfaces of base plate 404 and nerve root shield 406 apart, thereby engaging the end plates of the vertebrae and distracting the vertebrae apart from one another. Distraction may increase the distance between the two vertebra to facilitate subsequent insertion of one or more dynamic interbody devices (e.g., dynamic interbody devices 100' and 100") within the disc space. For example, distraction may be conducted to a distance that is about the same or greater than a height of the dynamic interbody device to be implanted. Dilator 422 may include proximal portion 422a, elongated portion 422b, and distal portion 422c. Proximal portion 422a of dilator 422 may have an inferior and/or superior surface with a shape that is substantially the same as the shape of an inferior and/or superior surface of a dynamic interbody device. Dilator 422 may be releasably coupled to elongated body 402 to distract the disc space. For example, in the illustrated embodiment, dilator 422 is inserted through slot 410 of elongated body 402 such that the proximal portion 422a of the dilator is located between an inferior/superior surface of base plate 404 and a superior/interior surface of shielding portion 406b of nerve root shield 406. During use, dilator 422 may be uncoupled from elongated body 402 and replaced with another dilator. For example, dilator 422 may be extracted from slot 410 of elongated body 402. Dilator 422 may include lip 424 and x-ray visible feature 426. Lip 424 may limit insertion of dilator 422 through slot 410. For example, in the illustrated embodiment, lip 424 may be located proximate distal end 422c of dilator 422 and may engage a complementary portion of elongated body 402, thereby preventing over-insertion of dilator 422 between base pate 404 and shielding portion 406, and the disc space. X-ray visible feature 426 may indicate the approximate expected location of the posterior edge of the dynamic interbody device. In some embodiments, x-ray visible feature 426 is radio-opaque. In some embodiments, dilator 422 may include one or more additional features that are visible via intra-operative techniques (e.g., x-ray, computed tomography, ultrasound, and magnetic resonance imaging).

When dilator 422 is positioned in slot 410, shielding portion 406b of nerve root shield 406 may be pressed against the end plate of the superior vertebra. Shielding portion 406b may protect the nerve root of the superior vertebra during the insertion of dilator 422. For example, shielding portion 406b may inhibit chafing of the nerve root by preventing direct contact between dilator 422 and the nerve root. In some embodiments, a surface of shielding portion 406b is shaped substantially complementary to a surface of the superior vertebra. Additionally, shielding portion 406b may have a superior surface with a shape that is substantially the same as the shape of a superior surface of the dynamic interbody device to be inserted in its place.

A guide frame 428 may couple two implant trials to one another during use, thereby fixing the positions of the implant trials relative to one another during use. Fixing the implant trials relative to one another may help to ensure that the dynamic interbody devices are disposed in desired positions relative to one another. FIG. 19 is a perspective view of guide frame 428 in accordance with one or more embodiments of the present technique. Guide frame 428 may include guide members 430, and insertion bridge 432 coupling the guide members. Insertion bridge 432 may include handle portion 432a and coupling portion 432b. Handle portion 432a may provide for grasping and manipulation of guide frame 428 by a user. Coupling portion 432b may provide for coupling of guide members 430 and instrumentation thereto.

Guide members 430 may be coupled to insertion bridge 432 such that the guide members are positioned at a selected convergent angle relative to one another. In various embodiments, guide members 430 are rigidly coupled to one another during use via coupling of each of guide members 430 to portion 432b of insertion bridge 432. In some embodiments, the convergent angle is about 45° between longitudinal axes of the guide members, or about 22.5° from a midline axis of insertion bridge 432. In some embodiments, the convergent angle is about 20° to 30° between longitudinal axes of the guide members, or about 10° to 15° from a midline axis of insertion bridge 432. In certain embodiments, the convergent angle is about 24° between longitudinal axes of the guide members, or about 12° from a midline axis of insertion bridge 432. In some embodiments, the position of one guide member is substantially mirrored by the other guide member. That is, the guide members are equally angled from a midline axis of insertion bridge 432.

Guide member 430 may include guide 434 and guide release 436. FIGS. 20 and 21 are top views of guide member 430 with guide release 436 in a first (locked) position and a second (unlocked) position, respectively, in accordance with one or more embodiments of the present technique. The internal shape of guide 434 may define an opening 434a. Opening 434a may be of any suitable shape or size. For example, in the illustrated embodiment, opening 434a includes a channel having a lateral opening. In some embodiments, opening 434a includes a laterally enclosed passage having a longitudinal opening. Opening 434a may be complementary to the external shape of a key of the proper corresponding implant trial or insertion instrument. As such, opening 434a may guide longitudinal movement of the implant trial or insertion instrument relative to guide frame 428. For example, the elongated body of an implant trial or insertion instrument may slide longitudinally through opening 434a of guide 434.

Figure 22:
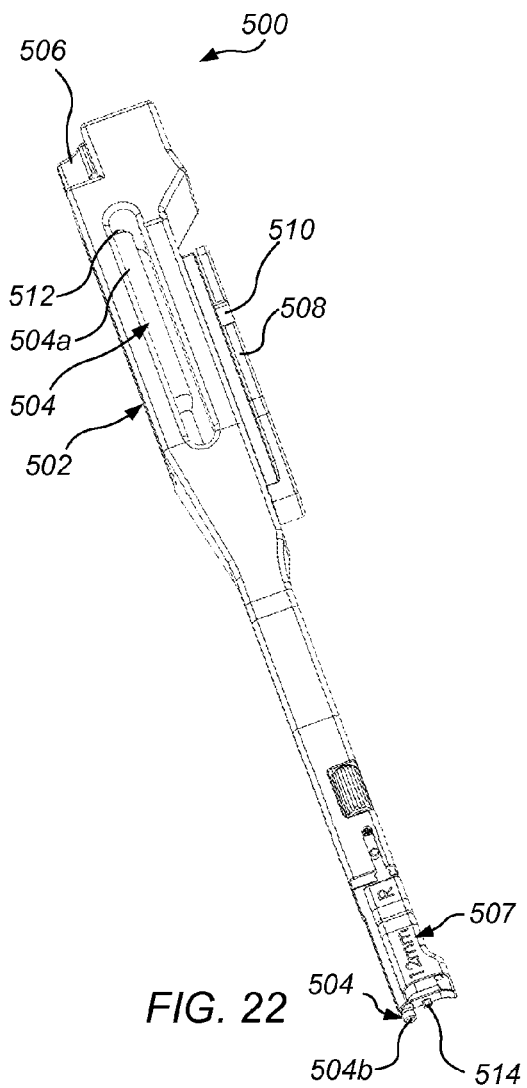
FIG. 22 is a perspective view of an insertion instrument in accordance with one or more embodiments of the present technique.
Figure 23:
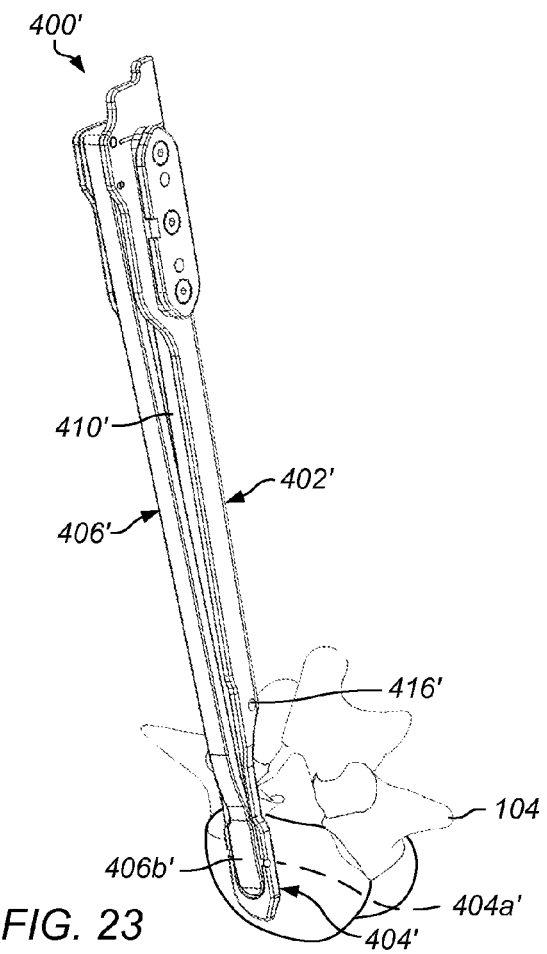
FIG. 23 is a perspective view of an implant trial having a base plate inserted into a disc space between vertebrae in accordance with one or more embodiments of the present technique.

Guide release 436 may include grip 438 and stop pin 440. Stop pin 440 may form a portion of a locking mechanism. Stop pin 440 in conjunction with one or more other of the locking mechanism may couple implant trial 400 to guide member 430 and fix the position of the implant trial relative to guide member 430. For example, stop pin 440 may protrude into the complementary pin catch of an implant trial 400. In a first (locked) position (depicted in FIG. 20), stop pin 440 may extend laterally into opening 434a of guide 434. For example, a spring or other bias member (not shown) may urge stop pin 440 into opening 434a. In a second (unlocked) position (depicted in FIG. 21), stop pin 440 may be pulled out of opening 434a via grip 438. With pin 440 in the unlocked position, implant trial 400 or similar instrumentation may be able to slide longitudinally though opening 434a, whereas, with pin 440 in the locked position, the implant trial 400 or similar instrumentation may be inhibited from sliding longitudinally though opening 434a FIG. 22 is a perspective view of an insertion instrument 500 in accordance with one or more embodiments of the present technique. In some embodiments, two cooperative dynamic interbody devices may be inserted between the vertebrae using one or more insertion instruments 500. For example, each of the dynamic interbody devices may be releasably coupled to a respective insertion instrument. In some embodiments, subsequent to distraction of the intervertebral space via the above described techniques, a first of the implant trials 400 is removed from opening 434a of guide frame 428 and replaced with a first insertion instrument 500 having a first dynamic interbody device coupled thereto, followed by a second of the implant trials 400 being removed from the other opening 434a of guide frame 428 and replaced with a second insertion instrument 500 having a second dynamic interbody device coupled thereto. In some embodiments, the insertion instrument for the second dynamic interbody device may be a mirror image of the insertion instrument for the first dynamic interbody device.

Insertion instrument 500 may include elongated body 502, insertion member 504, wheel 506, and insert(s) 507. Elongated body 502 may include key 508, pin catch 510, passageway 512, and ridge/protrusion 514. Key 508 may ensure that only the proper guide member can be used in association with the particular insertion instrument. For example, key 508 may have an external shape that is complementary to the internal shape (e.g., shape of opening 434a) of the proper guide member. In some embodiments, the proper guide member for the insertion instrument 500 may be the same guide member used in conjunction with implant trial 400. For example, the external shape of key 508 of insertion instrument 500 may be substantially the same as the external shape of key 408 of implant trial 400. Pin catch 510 may form a portion of a locking mechanism. Pin catch 510 in conjunction with one or more other portions of the locking mechanism may couple the insertion instrument to the guide member and fix the position of the insertion instrument relative to the guide member. For example, pin catch 510 may receive a complementary biased stop pin of the proper guide member. Insert 507 may provide for the adjustment of a height/thickness of insertion instrument 500 to match a specific height implant. For example, the illustrated embodiment, insert 507 labeled "12 mm" is designed for use with a 12 mm implant (e.g., interbody device 100', 100").

Insertion member 504 may be coupled to elongated body 502 of insertion instrument 500. For example, in the illustrated embodiment, insertion member 504 may be positioned within passageway 512 of elongated body 502. In some embodiments, insertion member 504 is telescopically coupled to elongated body 502. For example, in the illustrated embodiment, wheel 506 may be rotated to rotate insertion member 504. Rotating insertion member 504 may advance or retract the insertion member relative to the elongated body 502 of insertion instrument 500.

In some embodiments, insertion member 504 is provided with a substantially circular cross-section. For example, in the illustrated embodiment, insertion member 504 includes a cylindrical rod shaped member. Insertion member 504 may include a distal end 504a and a proximal end 504b. Distal end 504a of insertion member 504 may be coupled to wheel 506. Proximal end 504b of insertion member 504 may protrude from the proximal end of elongated body 502. Proximal end 504b of insertion member 504 may be threaded. An appropriate dynamic interbody device may be releasably coupled to insertion member 504. For example, proximal end 504b of insertion member 504 may mate with a threaded opening in the appropriate dynamic interbody device. Further, when proximal portion 504b of insertion member 504 is threaded to the appropriate dynamic interbody device, ridge 514 may reside in a corresponding slot of the dynamic interbody device to place the dynamic interbody device in the desired position for insertion (i.e., neutral axial rotation, neutral lateral bending, and full flexion).

Figure 36:
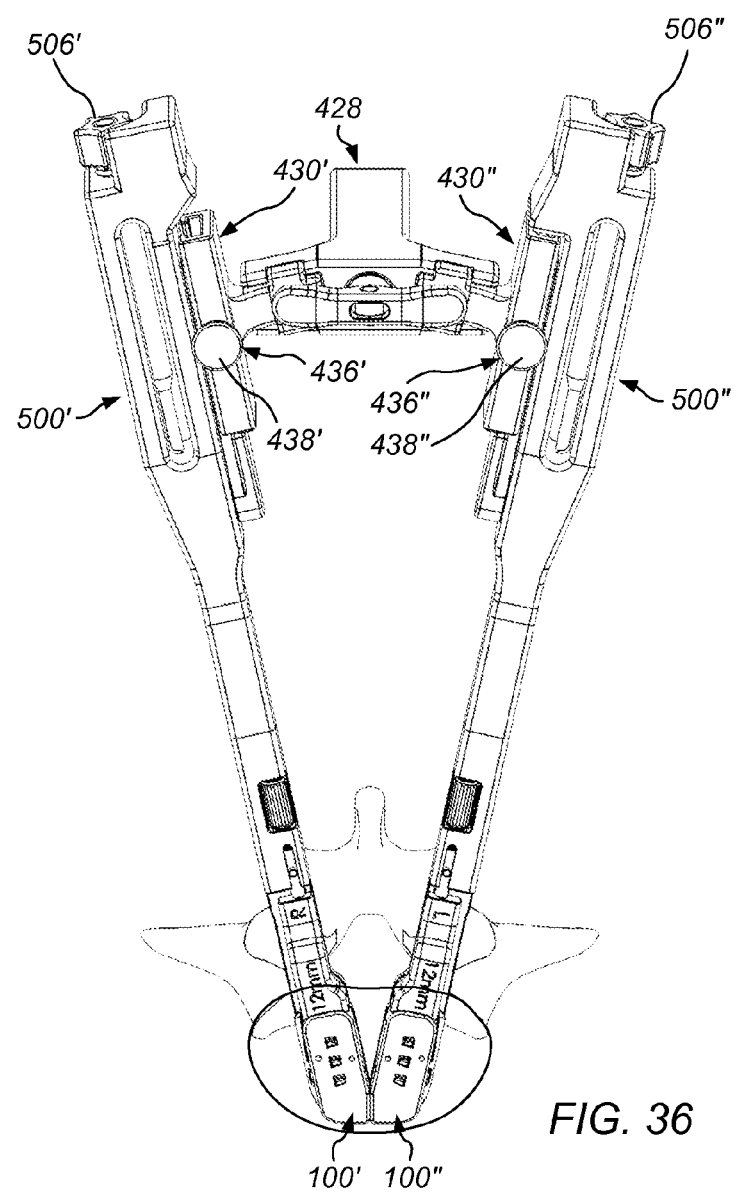
FIG. 36 is a front view of two insertion instruments coupled to respective dynamic interbody devices inserted into a disc space between vertebrae in accordance with one or more embodiments of the present technique.
Figure 37:
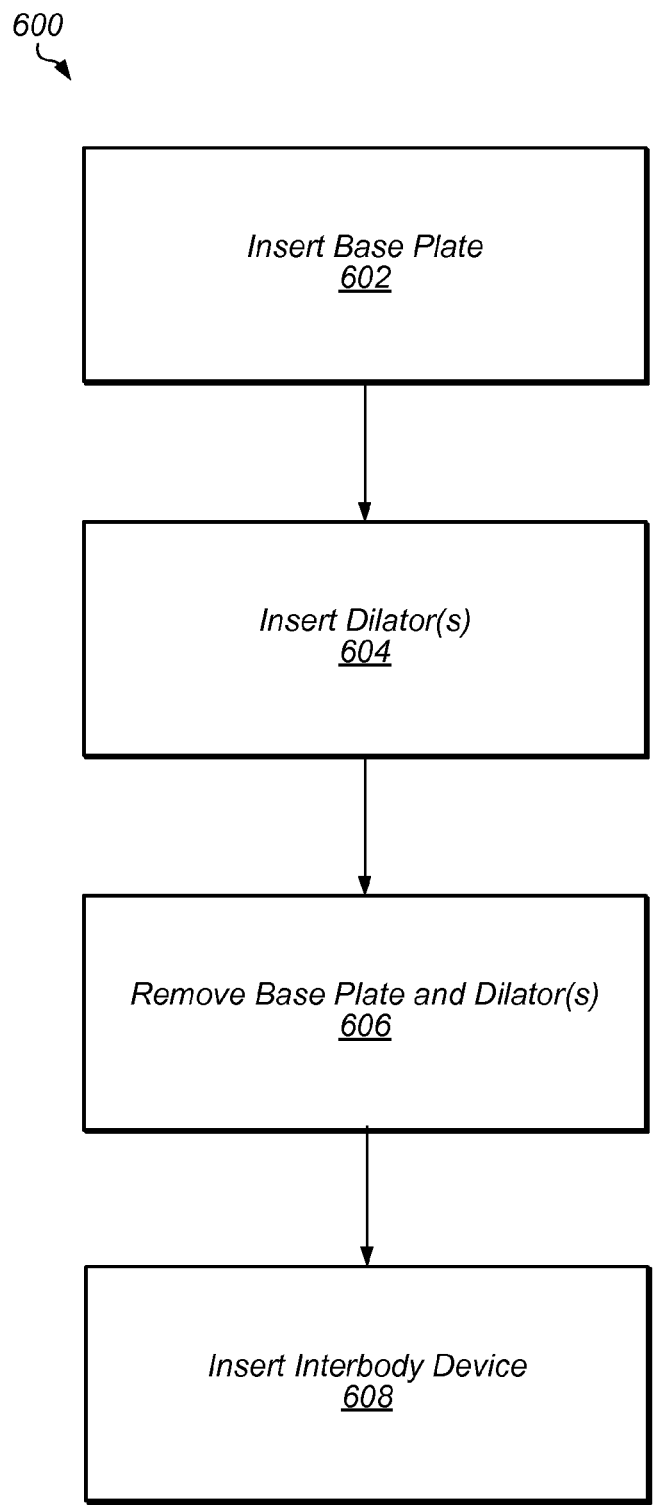
FIG. 37 is a flowchart that illustrates a method of inserting a dynamic interbody device into a disc space in accordance with one or more embodiments of the present technique.

FIGS. 23-36 illustrate a sequence of steps for inserting a dynamic interbody device into a disc space. FIG. 37 is a flowchart that illustrates a method 600 of inserting a dynamic interbody device into a disc space in accordance with one or more embodiments of the present technique. Although several embodiments are discussed with regard to dynamic interbody devices, the same or similar techniques may be employed for inserting other types of implants, such as spinal fusion implants. For example, the illustrated method may also be used for inserting one or more non-dynamic interbody devices (e.g., a pair of fusion interbody) into a disc space. Method 600 may generally include inserting a base plate of an implant trial into an intervertebral disc space; inserting one or more dilators into the disc space to achieve distraction of the disc space; removing the base plate and dilators from the disc space; and inserting the interbody device into the disc space in substantially the same position as the base plate.

In some embodiments, method 600 includes inserting a base plate of an implant trial into an intervertebral disc space, as depicted at block 602. Initially, when a dilator is not coupled to the elongated body (see FIG. 23), the implant trial may have a distraction height that is less than the separation height of the vertebrae, thereby allowing for insertion of base plate 404' into the disc space between vertebrae 104 and vertebrae 102 (not depicted in FIG. 23 for clarity). The distraction height may be measured as the distance between inferior surface 404a' of base plate 404' and the superior surface of shielding portion 406b' of nerve root shield 406'. The separation height 480 may be measured as the distance between the superior surface of inferior vertebra 104 and the inferior surface of superior vertebra 102 (see FIG. 26).

Base plate 404' of implant trial 400' may be selectively inserted and positioned at least partially within the disc space. For example, in the illustrated embodiment, base plate 404' is positioned at a selected anterior-posterior depth 444 (see FIG. 24). In some embodiments, base plate 404' may be inserted into the disc space until x-ray visible feature 418' is positioned at a selected distance from the anterior edge 104a of inferior vertebra 104. In some embodiments, base plate 404' may be inserted into the disc space substantially through a region bordered by the vertebral endplates, dura, and exiting nerve root (not shown) of the vertebrae. Base plate 404' may be positioned against the superior surface of inferior vertebra 104. Base plate 404' may be positioned within the disc space at a selected angle 450 with respect to the sagittal plane 452. In some embodiments, the selected angle is between about 10° to 14°. In certain embodiments, the selected angle is about 12°. Base plate 404' may be positioned within the disc space such that a portion of the base plate is on or near the sagittal plane. Positioning of base plate 404' may be confirmed by locating x-ray visible features 418', 420', and/or an additional feature of base plate 404' via intra-operative (e.g., x-ray, computed tomography, ultrasound, and magnetic resonance imaging). In some embodiments, lateral imaging techniques may be used to confirm that anterior-posterior depth of base plate 404'. Intra-operative equipment may be aligned with aperture 416' of implant trail 400' to obtain a true lateral image of the implant trial within the disc space.

In some embodiments, method 600 includes inserting one or more dilators to the disc space to achieve distraction of the disc space, as depicted at block 604. Proximal portion 422a' of dilator 422' may be inserted between the vertebrae to distract the disc space. For example, in the illustrated embodiment, dilator 422' may be removably inserted into slot 410' of implant trial 400' (see FIG. 25). Dilator 422' may be inserted into slot 410' until lip 424' is engaged with a portion of elongated body 402'. The height of dilator 422' may be such that shielding portion 406b' of nerve root shield 406' is pressed against the inferior face of superior vertebra 102 (see FIG. 26). X-ray visible feature 426' may be located less than about 5 millimeters (about 0.196 inches) from the posterior vertebral body edge 104b of inferior vertebra 104. The position of dilator 422' may be verified by locating x-ray visible feature 426' and/or an additional feature of dilator 422' via intra-operative (e.g., x-ray, computed tomography, ultrasound, and magnetic resonance imaging).

Guide member 430' of guide frame 428 may be placed proximate implant trial 400'. Guide member 430' may be coupled to implant trial 400'. For example, in the illustrated embodiment, grip 438' of guide release 436' may be pulled outwards to withdraw a stop pin from opening 434a' of guide 434'; guide 434' may then be engaged with key 408' of elongated body 402' (see FIG. 27). In some embodiments, guide 434' is laterally engaged with key 408'. In some embodiments, guide 434' is longitudinally engaged with key 408'. Grip 438' may be released so that a spring in guide release 436' urges the stop pin against key 408'. Once engaged, guide member 430' may be lowered along key 408' until the stop pin extends into pin catch 412'. In some embodiments, elongated body 402' is slidable through opening 434a' of guide 434'.

Figure 28:
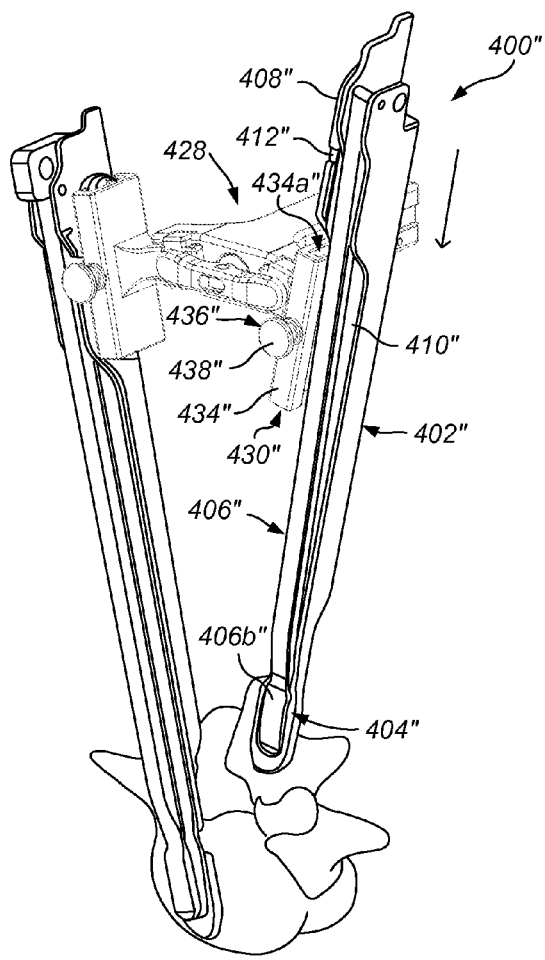
FIG. 28 is a perspective view of a second implant trial being coupled to a second guide member in accordance with one or more embodiments of the present technique.
Figure 29:
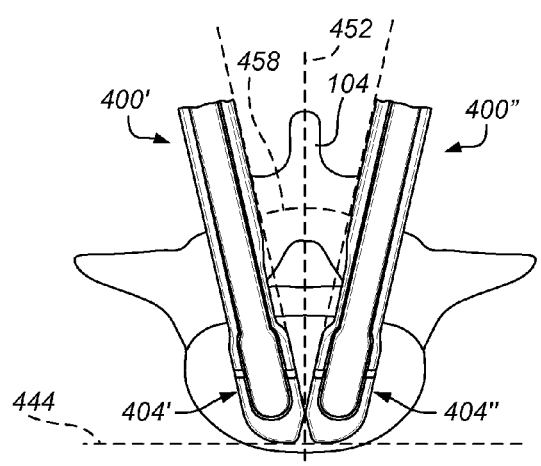
FIG. 29 is a front view of lower portions of the two implant trials having respective base plates inserted into a disc space between vertebrae in accordance with one or more embodiments of the present technique.

Implant trial 400" may be placed proximate second guide member 430" of guide frame 428 (see FIG. 28). Implant trial 400" may be coupled to guide member 430". For example, in the illustrated embodiment, grip 438" of guide release 436" may be pulled outwards to withdraw a stop pin from opening 434a" of guide 434"; key 408" may then be engaged with guide 434". In some embodiments, key 408" is laterally engaged with guide 434". In some embodiments, key 408" is longitudinally engaged with guide 434". Grip 438" may be released so that a spring in guide release 436" urges the stop pin against key 408". Once engaged, implant trial 400" may be lowered along guide 434" until the stop pin extends into pin catch 412". In some embodiments, elongated body 402" is slidable through opening 434a" of guide 434".

The position of base plate 404" within the disc space may substantially mirror the position of base plate 404' within the disc space. As such, a portion of base plate 404" may abut or be close to abutting the portion of base plate 404' on or near the sagittal plane 452 (see FIG. 29). Angle 458 between the abutting portions of base plates 404' and 404" may be equal to the convergent angle of the guide members. In some embodiments, angle 458 is about 20° to 30°. In certain embodiments, angle 458 is about 24°. In some embodiments, the base plates of the expandable trials may be coupled together with male and female portions when the base plates are positioned between the vertebrae. In some embodiments, base plates 404' and 404" are positioned at a selected, substantially equal anterior-posterior depth 444. Positioning of base plates 404', 404" may be confirmed via intra-operative (e.g., x-ray, computed tomography, ultrasound, and magnetic resonance imaging).

The proximal portion of a second dilator may be inserted between the vertebrae to further distract the disc space. For example, the second dilator may be removably inserted into slot 410" of implant trial 400". The height of the second dilator may be such that shielding portion 406b" of nerve root shield 406" is firmly pressed against the inferior face of superior vertebra 102. The dilators inserted into the disc space may be sequentially removed and replaced one after the other with progressively larger dilators until a maximum separation height is achieved. A maximum separation height may be achieved when the disc space opens posteriorly without parallel anterior separation. The separation height 480 between the vertebrae may be verified via lateral x-ray imaging. In some embodiments, the size of a dynamic interbody device to be implanted within the disc space is determined according to the maximum separation height. In some embodiments, a height of the interbody device is less than or equal to the maximum separation height achieved via distraction. For example, the height of a dynamic interbody device may be about 2 millimeters (about 0.079 inches) or less than the maximum separation height achieved via distraction.

Figure 30:
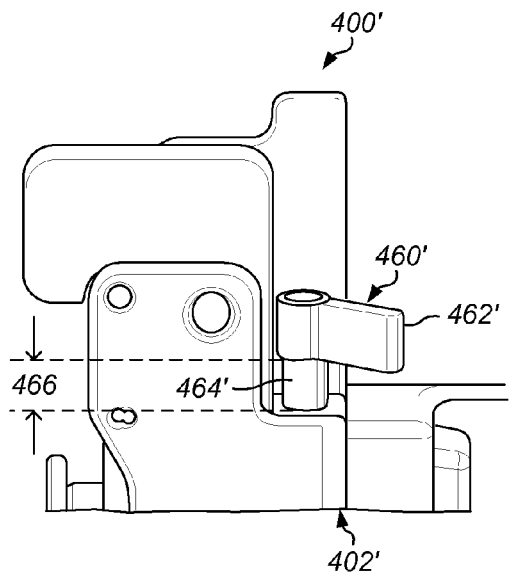
FIG. 30 is a perspective view of an upper portion of the implant trial of FIG. 23 including a drill guide in accordance with one or more embodiments of the present technique.
Figure 31:
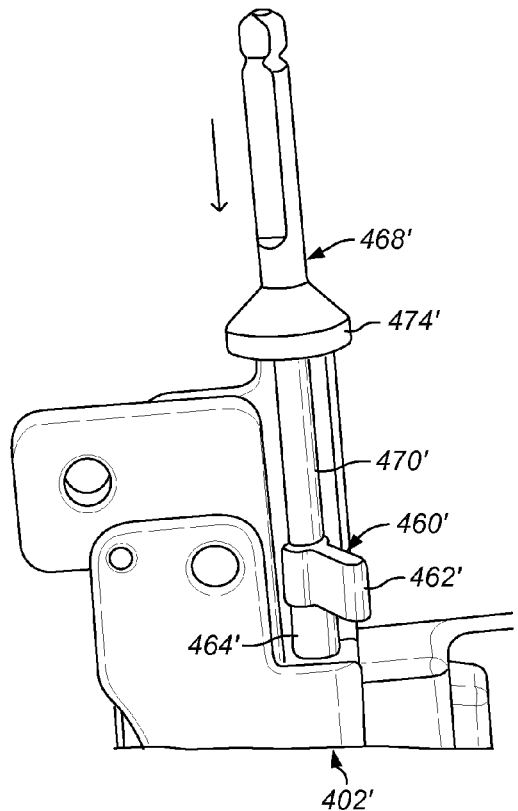
FIG. 31 is a perspective view of an upper portion of the implant trial of FIG. 23 depicting a anchor guide being inserted into the disc space in accordance with one or more embodiments of the present technique.
Figure 32:
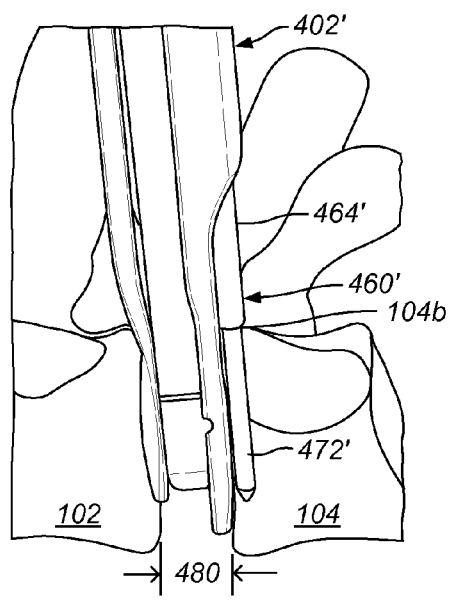
FIG. 32 is a side view of a lower portion of the implant trial of FIG. 23 having a base plate inserted into a disc space between vertebrae and including drill and anchor guides in accordance with one or more embodiments of the present technique.
Figure 33:
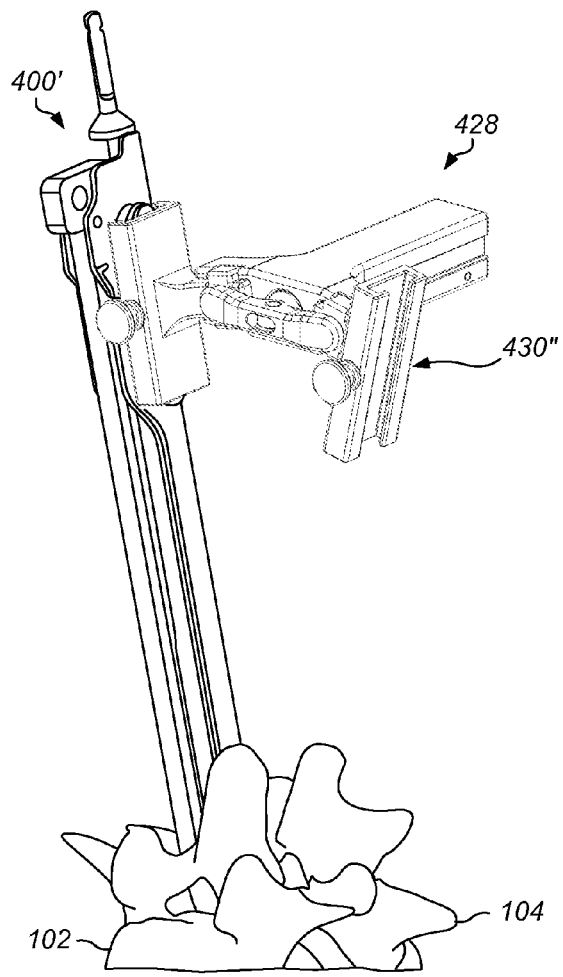
FIG. 33 is a perspective view of the implant trial of FIG. 23 including drill and anchor guides having a base plate inserted into a disc space between vertebrae and coupled to a guide member in accordance with one or more embodiments of the present technique.
Figure 34:
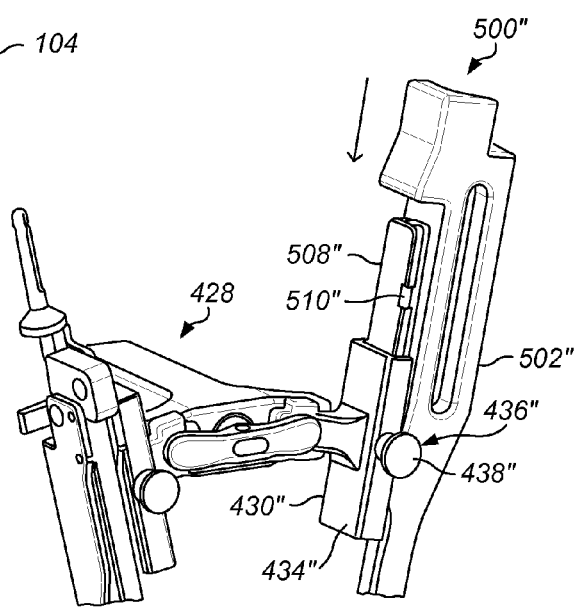
FIG. 34 is a perspective view of a top portion of an insertion instrument being coupled to a guide member in accordance with one or more embodiments of the present technique.
Figure 35:
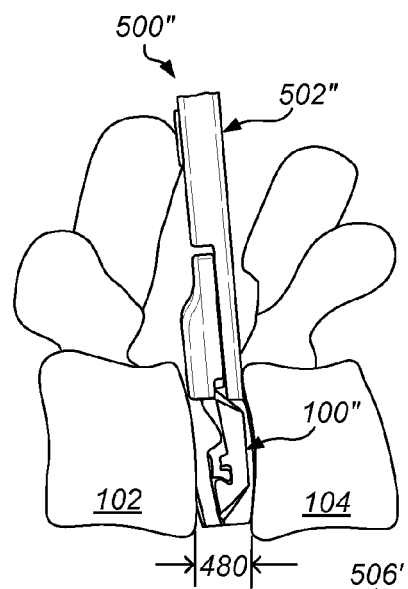
FIG. 35 is a side view of lower portion of the insertion instrument of FIG. 34 coupled to a dynamic interbody device inserted into a disc space between vertebrae in accordance with one or more embodiments of the present technique.

A drill guide 460' may be positioned in a groove of implant trial 400' (see FIG. 30). Drill guide 460' may include flag 462' and tubular body 464'. The proximal end of drill guide 460' may abut the posterior vertebral body edge 104b of inferior vertebra 104. Flag 462' may be located at the distal end of the drill guide. The distance 466 between flag 462' and a surface of elongated body 402' may indicate the approximate expected distance between the posterior end of the dynamic interbody device and the posterior vertebral body edge 104b of inferior vertebra 104.

A anchor guide 468' may be inserted through tubular body 464' of drill guide 460' to form an aperture in inferior vertebra 104 for the anchor of the dynamic interbody device (see FIG.

31). Anchor guide 468' may include shaft 470', drill bit 472', and drill stop 474'. Shaft 470' may extend drill bit 472' through tubular body 464' and into the disc space. Drill bit 472' may pierce the vertebral body of the inferior vertebra 104, thereby forming an aperture (see FIG. 32) in the inferior vertebra. Drill stop 474', located near the distal end of the anchor guide, may abut a portion of elongated body 402 to prevent boring of the vertebral body passed a selected depth. Similar drill and anchor guides may be used in conjunction with implant trial 400" to form a second aperture in the vertebral body of the inferior vertebra 104.

In some embodiments, method 600 removing the base plate and dilators from the disc space, as depicted at block 606. A dilator may be removed from the disc space and slot 410" to decrease the distraction height of implant trial 400". Implant trial 400" may be uncoupled from guide member 430" of guide frame 428. For example, in the illustrated embodiment, grip 438" of guide release 436" may be pulled outwards to withdraw the stop pin from guide 434". Implant trial 400" may then be removed from the disc space and guide member 430". Base plate 404" of implant trial 400" may be removed from the disc space while base plate 404' of implant trial 400' remains at least partially inserted in the disc space (see FIG. 33).

In some embodiments, method 600 includes inserting the interbody device into the disc space in substantially the same position as the base plate, as depicted at block 608. Insertion instrument 500" coupled to dynamic interbody device 100" may be placed proximate guide member 430" of guide frame 428. Elongated body 502" of insertion instrument 500" may be coupled to guide member 430". For example, in the depicted embodiment, grip 438" of guide release 436" may be pulled outwards to withdraw the stop pin from the opening of guide 434"; key 508" may be engaged with guide 434" (see FIG. 34). In some embodiments, key 508" is laterally engaged with guide 434". In some embodiments, key 508" is longitudinally engaged with guide 434". Grip 438' may then be released so that the spring in guide release 436" urges the stop pin against key 508". Once engaged, insertion instrument 500" may be lowered through guide 434" until the stop pin extends into pin catch 510". Anchor 116 of dynamic interbody device 100" may be received by the aperture formed in inferior vertebra 104. If needed, a mallet or other impact instrument may be driven against a distal end of insertion instrument 500" to drive dynamic interbody device 100" between the vertebrae (see FIG. 35).

Implant trial 400' may be removed from the disc space and guide member 430' of guide frame 428. Insertion instrument 500' coupled to dynamic interbody device 100' may be inserted in a similar manner as that described above with respect to insertion instrument 500" and dynamic interbody device 100". FIG. 36 depicts insertion instruments 500', 500" and dynamic interbody devices 100', 100" positioned in the disc space. Positioning of dynamic interbody devices 100', 100" may be confirmed via intra-operative (e.g., x-ray, computed tomography, ultrasound, and magnetic resonance imaging). In some embodiments, when the dynamic interbody devices 100', 100" are properly interconnected and positioned, insertion members 504', 504" may be uncoupled from the respective portions of the dynamic interbody devices 100', 100". For example, in the illustrated embodiment, wheels 506', 506" of insertion instruments 500', 500" may be rotated to withdraw insertion members 504', 504" from openings 144 of dynamic interbody devices 100', 100". Grips 438', 438" of guide members 430', 430" may be pulled outwards to retract the stop pins of the guide releases 436', 436" from channels 434', 434", and insertion instruments 500', 500" may be removed from the disc space and guide members. It will be appreciated that the above described techniques are illustrative, and modifications thereto may be within the scope of this disclosure. For example, in some embodiments, implant trial 400' may be removed and insertion instrument 500' and dynamic interbody device 100' may be installed prior to removal of implant trial 400" and installation of insertion instrument 500" and dynamic interbody device 100". In some embodiments, insertion bridge 428 and/or guide frame 432 may be removed prior to removal of insertion instruments 500', 500".

Additional techniques that may be used to insert dynamic interbody devices between vertebrae are described in U.S. Patent Publication No. 2009/0105829 to Gimbel et al.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims. Furthermore, note that the word "may" is used throughout this application in a permissive sense (i.e., having the potential to, being able to), not a mandatory sense (i.e., must). The term "include", and derivations thereof, mean "including, but not limited to". As used throughout this application, the singular forms "a", "an" and "the" include plural referents unless the content clearly indicates otherwise. Thus, for example, reference to "a member" includes a combination of two or more members. The term "coupled" means "directly or indirectly connected".

In this patent, certain U.S. patents, and U.S. patent applications have been incorporated by reference. The text of such U.S. patents and U.S. patent applications is, however, only incorporated by reference to the extent that no conflict exists between such text and the other statements and drawings set forth herein. In the event of such conflict, then any such conflicting text in such incorporated by reference U.S. patents and U.S. patent applications is specifically not incorporated by reference in this patent.

What is claimed is:

1. A method of implanting an interbody device into a disc space located between a first and second vertebra, comprising:

inserting a base plate of a first implant trial into the disc space;

inserting a base plate of a second implant trial into the disc space, wherein the second implant trial is coupled to the first implant trial to position the base plate of the first implant trial relative to the base plate of the second implant trial;

inserting one or more dilators into the disc space proximate the base plates of the first or second implant trials to distract the first and second vertebrae;

removing the base plate of the first implant trial and the dilators from the disc space; and inserting the interbody device into the disc space in substantially the same position as the base plate of the first implant trial.

2. The method of claim 1, wherein inserting a base plate of a first implant trial into the disc space comprises inserting the base plate to a selected location within the disc space, and wherein the selected location comprises a selected angle with respect to the sagittal plane of the vertebrae.

3. The method of claim 1, wherein the first and second implant trials are coupled via a guide frame.

4. The method of claim 3, wherein the guide frame comprises first and second guide members and wherein the first implant trial is coupled to the first guide member and the second implant trial is coupled to the second guide member.

5. The method of claim 4, wherein the first and second guide members comprise respective openings, and wherein inserting a base plate of the second implant trial into the disc space comprises longitudinal movement of the second implant trial through the opening of the second guide member.

6. The method of claim 1, wherein at least one of the implant trials comprises a nerve root shield, and wherein inserting one or more dilators into the disc space comprises inserting the dilators between the base plate and the nerve root shield.

7. The method of claim 6, wherein the nerve root shield comprises a surface that is shaped complementary to a surface of the respective implant trial.

8. The method of claim 1, wherein inserting one or more dilators into the disc space comprises inserting progressively larger dilators into the disc space until the disc space opens posteriorly without parallel anterior separation.

9. The method of claim 1, wherein the second implant trial is coupled to the first implant trial such that the base plates of the first and second implant trials abut substantially at or near the sagittal plane of the vertebrae.

10. A method of implanting interbody devices into a disc space located between a first and second vertebra, comprising:
   inserting a base plate of a first implant trial to a selected location at least partially within the disc space, the first implant trial comprising an elongated body and a base plate coupled to the elongated body,
      wherein the selected location comprises a selected angle with respect to the sagittal plane of the vertebrae;
   inserting a first dilator between the base plate of the first implant trial and the first or second vertebra to distract the vertebrae;
   coupling a first guide member of a guide frame to the elongated body of the first implant trial, the guide frame further comprising a second guide member and wherein the first and second guide members of the guide frame are rigidly coupled and positioned at a selected convergent angle relative to one another;
   coupling an elongated body of a second implant trial to the second guide member such that a base plate of the second implant trial is inserted at least partially within the disc space, and such that at least a portion of the base plate of the second implant trial abuts a portion of the base plate of the first implant trial;
   inserting a second dilator between the base plate of the second implant trial and the endplate of the first or second vertebra to distract the vertebrae;
   removing the base plate of the first implant trial and the first dilator from the disc space and uncoupling the elongated body of the first implant trial from the first guide member;
   coupling an elongated body of a first insertion instrument to the first guide member such that a first interbody device is inserted at least partially within the disc space in substantially the same position as the base plate of the first implant trial, the first insertion instrument comprising the elongated body and an insertion member coupled to the elongated body, wherein the insertion member is releasably coupled to the first interbody device,
      wherein the first interbody device is positioned within the disc space at a selected angle with respect to the sagittal plane of the vertebra;
   removing the base plate of the second implant trial and the second dilator from the disc space and uncoupling the elongated body of the second implant trial from the second guide member;
   coupling an elongated body of a second insertion instrument to the second guide member such that a second interbody device is inserted at least partially within the disc space in substantially the same position as the base plate of the second implant trial, the second insertion instrument comprising an elongated body and an insertion member coupled to the elongated body, wherein the insertion member is releasably coupled to the second interbody device,
      wherein at least a portion of the second interbody device is located at or near the first interbody device;
   uncoupling the first interbody device from the insertion member of the first insertion instrument; and
   uncoupling the second interbody device from the insertion member of the second insertion instrument.

11. The method of claim 10, wherein the first and second implant trials and the first and second insertion instruments are at least partially inserted into the disc space substantially through the region bordered by the vertebral endplates of the first and second vertebrae, dura, and exiting nerve root of the first and second vertebrae.

12. The method of claim 10, wherein the base plates of the first and second implant trials abut substantially at or near the sagittal plane of the vertebrae.

13. The method of claim 10, wherein at least one of the first and second implant trials comprises a nerve root shield, and wherein inserting a first or second dilator comprises inserting the dilator between the base plate and the nerve root shield of the respective implant trial.

14. The method of claim 13, wherein the nerve root shield comprises a surface that is shaped complementary to a surface of the first or second vertebra.

15. The method of claim 10, wherein at least one of the dilators or one of the base plates of the first and second implant trials comprises an x-ray visible feature indicating an expected approximate location of a posterior edge of the interbody device, and
   wherein the selected location further comprises a selected distance measured from the expected approximate location of the posterior edge of the interbody device to the posterior vertebral body edge of the first and/or second vertebra.

16. The method of claim 10, wherein the base plates of the first and second implant trials each comprise an x-ray visible feature indicating an expected approximate location of a center of rotation of the interbody device, and
   wherein the elongated body of a second implant trial is coupled to the second guide member such that the x-ray visible features of the base plates of the first and second implant trials are located at a substantially equal anterior-posterior depth within the disc space.

17. The method of claim 10, wherein at least one of the base plates of the first and second implant trials comprises an x-ray visible feature indicating an expected approximate location of an anterior edge of the interbody device, and wherein the selected location further comprises a selected distance measured from the expected approximate location of the anterior edge of the interbody device to the anterior edge of the first and/or second vertebra.

18. The method of claim 10, wherein inserting a first or second dilator comprises inserting progressively larger dilators at least partially into the disc space between the base plate of the first and second implant trials respectively and the first or second vertebra until the disc space opens posteriorly without parallel anterior separation.

19. The method of claim 18, wherein the disc height achieved at which the disc space opens posteriorly without parallel anterior distraction is the maximum separation height of the disc space.

20. The method of claim 19, wherein the height of the interbody device is less than the maximum achieved separation height of the disc space.

21. The method of claim 10, wherein the elongated bodies are laterally engaged with the respective guide members.

* * * * *